(12) United States Patent
Pui et al.

(10) Patent No.: US 8,028,646 B2
(45) Date of Patent: Oct. 4, 2011

(54) COATING MEDICAL DEVICES

(75) Inventors: David Y. H. Pui, Plymouth, MN (US); Da-Ren Chen, Creve Coeur, MO (US)

(73) Assignee: Regents of the University of Minnesota, St. Paul, MN (US)

( * ) Notice: Subject to any disclaimer, the term of this patent is extended or adjusted under 35 U.S.C. 154(b) by 1265 days.

(21) Appl. No.: 11/390,606

(22) Filed: Mar. 28, 2006

(65) Prior Publication Data
US 2006/0177573 A1   Aug. 10, 2006

Related U.S. Application Data

(60) Division of application No. 10/301,473, filed on Nov. 21, 2002, now Pat. No. 7,247,338, which is a continuation-in-part of application No. 09/858,865, filed on May 16, 2001, now Pat. No. 6,764,720.

(51) Int. Cl.
*B05C 7/02* (2006.01)

(52) U.S. Cl. ....... 118/50.1; 118/622; 118/626; 118/629; 118/308; 118/315

(58) Field of Classification Search ............... 118/50.1, 118/620, 622, 626, 629, 308, 313, 315, 500; 427/2.24, 2.25, 2.28; 239/690, 695, 696; 623/1.46, 1.47, 1.48
See application file for complete search history.

(56) References Cited

U.S. PATENT DOCUMENTS

| 3,001,890 | A | * | 9/1961 | Sedlacsik, Jr. .......... 427/484 |
| 3,521,125 | A | | 7/1970 | Nelson |
| 3,608,823 | A | | 9/1971 | Buschor |
| 3,654,534 | A | | 4/1972 | Fischer |
| 3,905,330 | A | | 9/1975 | Coffee |
| 4,002,777 | A | | 1/1977 | Juvinall et al. |

(Continued)

FOREIGN PATENT DOCUMENTS

CA   2 435 721   8/2002

(Continued)

OTHER PUBLICATIONS

Jouyban et al., "A simple relationship between dielectric constant of mixed solvents with solvent composition and temperature," 2004, Int. Journ. Of Pharamceutics, 269:353-360.

(Continued)

*Primary Examiner* — Laura Edwards
(74) *Attorney, Agent, or Firm* — Mueting Raasch & Gebhardt, P.A.

(57) ABSTRACT

Methods and systems for coating at least a portion of a medical device (e.g., a stent structure) include providing a plurality of coating particles (e.g., monodisperse coating particles) in a defined volume. For example, the particles may be provided using one or more nozzle structures, wherein each nozzle structure includes at least one opening terminating at a dispensing end. The plurality of coating particles may be provided in the defined volume by dispensing a plurality of microdroplets having an electrical charge associated therewith from the dispensing ends of the one or more nozzle structures through use of a nonuniform electrical field between the dispensing ends and the medical device. Electrical charge is concentrated on the particle as the microdroplet evaporates. With a plurality of coating particles provided in the defined volume, such particles can be moved towards at least one surface of the medical device to form a coating thereon (e.g., using an electric field and/or a thermoph

U.S. PATENT DOCUMENTS

| | | | |
|---|---|---|---|
| 4,039,145 A | 8/1977 | Felici et al. | |
| 4,265,641 A | 5/1981 | Natarajan | |
| 4,328,940 A | 5/1982 | Malcolm | |
| 4,414,603 A | 11/1983 | Masuda | |
| 4,476,515 A | 10/1984 | Coffee | |
| 4,578,290 A | 3/1986 | Komon et al. | |
| 4,634,057 A | 1/1987 | Coffee et al. | |
| 4,659,012 A | 4/1987 | Coffee | |
| 4,748,043 A | 5/1988 | Seaver et al. | |
| 4,749,125 A | 6/1988 | Escallon et al. | |
| 4,795,330 A | 1/1989 | Noakes et al. | |
| 4,846,407 A | 7/1989 | Coffee et al. | |
| 4,878,454 A * | 11/1989 | Cann | 118/663 |
| 4,945,050 A | 7/1990 | Sanford et al. | |
| 4,946,899 A | 8/1990 | Kennedy et al. | |
| 5,036,006 A | 7/1991 | Sanford et al. | |
| 5,044,564 A | 9/1991 | Sickles | |
| 5,066,587 A | 11/1991 | Jones et al. | |
| 5,091,205 A | 2/1992 | Fan | |
| 5,100,792 A | 3/1992 | Sanford et al. | |
| 5,120,657 A | 6/1992 | McCabe et al. | |
| 5,141,131 A | 8/1992 | Miller, Jr. et al. | |
| 5,149,655 A | 9/1992 | McCabe et al. | |
| 5,179,022 A | 1/1993 | Sanford et al. | |
| 5,204,253 A | 4/1993 | Sanford et al. | |
| 5,219,746 A | 6/1993 | Brinegar et al. | |
| 5,222,663 A | 6/1993 | Noakes et al. | |
| 5,240,842 A | 8/1993 | Mets | |
| 5,247,842 A | 9/1993 | Kaufman et al. | |
| 5,354,556 A | 10/1994 | Sparks et al. | |
| 5,371,015 A | 12/1994 | Sanford et al. | |
| 5,433,865 A | 7/1995 | Laurent | |
| 5,457,041 A | 10/1995 | Ginaven et al. | |
| 5,464,650 A | 11/1995 | Berg et al. | |
| 5,475,228 A | 12/1995 | Palathingal | |
| 5,478,744 A | 12/1995 | Sanford et al. | |
| 5,506,125 A | 4/1996 | McCabe et al. | |
| 5,516,670 A | 5/1996 | Kuehnle et al. | |
| 5,525,510 A | 6/1996 | McCabe et al. | |
| 5,549,755 A * | 8/1996 | Milovich et al. | 118/629 |
| 5,584,807 A | 12/1996 | McCabe | |
| 5,621,605 A | 4/1997 | Inaba et al. | |
| 5,655,517 A | 8/1997 | Coffee | |
| 5,683,556 A | 11/1997 | Nomura et al. | |
| 5,685,482 A | 11/1997 | Sickles | |
| 5,702,754 A | 12/1997 | Zhong | |
| 5,807,436 A | 9/1998 | Stachelhaus et al. | |
| 5,813,614 A | 9/1998 | Coffee | |
| 5,837,313 A | 11/1998 | Ding et al. | |
| 5,846,595 A | 12/1998 | Sun et al. | |
| 5,866,400 A | 2/1999 | Palsson et al. | |
| 5,873,523 A | 2/1999 | Gomez et al. | |
| 5,897,911 A | 4/1999 | Loeffler | |
| 5,915,377 A | 6/1999 | Coffee | |
| 5,973,904 A | 10/1999 | Pui et al. | |
| 5,980,972 A | 11/1999 | Ding | |
| 5,992,244 A | 11/1999 | Pui et al. | |
| 6,056,993 A * | 5/2000 | Leidner et al. | 427/2.25 |
| 6,068,199 A | 5/2000 | Coffee | |
| 6,074,688 A | 6/2000 | Pletcher et al. | |
| 6,093,557 A | 7/2000 | Pui et al. | |
| 6,096,070 A | 8/2000 | Ragheb et al. | |
| 6,105,571 A | 8/2000 | Coffee | |
| 6,105,877 A | 8/2000 | Coffee | |
| 6,120,847 A | 9/2000 | Yang et al. | |
| 6,126,086 A | 10/2000 | Browner et al. | |
| 6,143,370 A | 11/2000 | Panagiotou et al. | |
| 6,145,391 A | 11/2000 | Pui et al. | |
| 6,251,136 B1 | 6/2001 | Guruwaiya et al. | |
| 6,252,129 B1 | 6/2001 | Coffee | |
| 6,318,640 B1 | 11/2001 | Coffee | |
| 6,364,903 B2 | 4/2002 | Tseng et al. | |
| 6,368,658 B1 | 4/2002 | Schwarz et al. | |
| 6,386,195 B1 | 5/2002 | Coffee | |
| 6,399,362 B1 | 6/2002 | Pui et al. | |
| 6,419,692 B1 | 7/2002 | Yang et al. | |
| 6,419,745 B1 | 7/2002 | Burkett et al. | |
| 6,457,470 B1 | 10/2002 | Coffee | |
| 6,517,888 B1 | 2/2003 | Weber | |
| 6,565,659 B1 * | 5/2003 | Pacetti et al. | 118/500 |
| 6,595,208 B1 | 7/2003 | Coffee et al. | |
| 6,669,980 B2 | 12/2003 | Hansen | |
| 6,684,879 B1 | 2/2004 | Coffee et al. | |
| 6,695,920 B1 * | 2/2004 | Pacetti et al. | 118/500 |
| 6,743,463 B2 | 6/2004 | Weber et al. | |
| 6,746,869 B2 | 6/2004 | Pui et al. | |
| 6,764,720 B2 | 7/2004 | Pui et al. | |
| 6,861,088 B2 | 3/2005 | Weber et al. | |
| 6,989,169 B2 | 1/2006 | Ripoll et al. | |
| 7,193,124 B2 | 3/2007 | Coffee | |
| 7,247,338 B2 | 7/2007 | Pui | |
| 7,279,322 B2 | 10/2007 | Pui et al. | |
| 7,498,063 B2 | 3/2009 | Pui et al. | |
| 2002/0004101 A1 | 1/2002 | Ding et al. | |
| 2002/0007869 A1 | 1/2002 | Pui | |
| 2002/0065553 A1 | 5/2002 | Weber | |
| 2003/0082324 A1 * | 5/2003 | Sogard et al. | 428/36.9 |
| 2003/0143315 A1 | 7/2003 | Pui et al. | |
| 2003/0161937 A1 | 8/2003 | Leiby et al. | |
| 2003/0236514 A1 | 12/2003 | Schwarz | |
| 2004/0069632 A1 | 4/2004 | Ripoll et al. | |
| 2004/0161498 A1 | 8/2004 | Ripoll et al. | |
| 2004/0177807 A1 | 9/2004 | Pui et al. | |
| 2004/0200729 A1 | 10/2004 | Boulais et al. | |
| 2004/0234748 A1 | 11/2004 | Stenzel | |
| 2004/0241315 A1 | 12/2004 | Pui et al. | |
| 2005/0116070 A1 | 6/2005 | Ganan Calvo et al. | |
| 2005/0175772 A1 | 8/2005 | Worsham et al. | |
| 2006/0057259 A1 | 3/2006 | Ripoll et al. | |
| 2007/0199824 A1 | 8/2007 | Pui | |
| 2007/0278103 A1 | 12/2007 | Hoerr et al. | |
| 2008/0210302 A1 | 9/2008 | Gupta | |
| 2009/0266924 A1 | 10/2009 | Pui | |

FOREIGN PATENT DOCUMENTS

| | | |
|---|---|---|
| CA | 2 436 524 | 8/2002 |
| CH | 550 022 A | 6/1974 |
| CN | 1052695 A | 3/1993 |
| DE | 198 46 656 A1 | 4/1999 |
| DE | 199 09 333 A1 | 11/1999 |
| EP | 01 0234841 A2 | 9/1987 |
| EP | 0 270 356 A2 | 12/1987 |
| EP | 0 258 016 A1 | 3/1988 |
| EP | 0 258 016 B1 | 3/1988 |
| EP | 0 434 616 | 12/1990 |
| EP | 0 405 884 A | 1/1991 |
| EP | 0 429 234 A2 | 5/1991 |
| EP | 0 429 234 A3 | 5/1991 |
| EP | 0 429 234 B1 | 5/1991 |
| EP | 0 434 616 A1 | 6/1991 |
| EP | 0 434 616 B1 | 6/1991 |
| EP | 1 355 537 A1 | 8/2002 |
| EP | 1 364 718 A1 | 11/2003 |
| ES | 2 180 405 | 2/2003 |
| JP | 6-242273 | 9/1994 |
| JP | 11-500047 | 1/1999 |
| JP | 11-199471 | 7/1999 |
| JP | 2004 531365 | 10/2004 |
| MX | 03006862 A | 10/2004 |
| WO | 91/00915 | 1/1991 |
| WO | 91/07487 | 5/1991 |
| WO | 93/07465 | 4/1993 |
| WO | 94/12285 | 6/1994 |
| WO | 97/10011 | 3/1997 |
| WO | 97/49484 | 12/1997 |
| WO | 98/03267 | 1/1998 |
| WO | 98/42446 | 10/1998 |
| WO | 98/56894 | 12/1998 |
| WO | 99/03517 | 1/1999 |
| WO | 99/30812 | 6/1999 |
| WO | 99/30835 | 6/1999 |
| WO | 99/31019 | 6/1999 |
| WO | 01/87491 A1 | 11/2001 |
| WO | 02/060275 A1 | 8/2002 |
| WO | 02/060591 A1 | 8/2002 |
| WO | 03/082363 A1 | 10/2003 |
| WO | 2004/047882 A2 | 6/2004 |

| WO | 2006/086654 |    | 8/2006 |
|----|-------------|----|--------|
| WO | 2007/089881 | A2 | 8/2007 |
| WO | 2007/089881 | A3 | 8/2007 |
| WO | 2007/089883 | A2 | 8/2007 |
| WO | 2008/094700 | A3 | 8/2008 |
| WO | 2008094700  | A2 | 8/2008 |

OTHER PUBLICATIONS

Adachi et al., "High-efficiency unipolar aerosol charger using a radioactive alpha source," *Aerosol Science, Industry Health and Environment*, Masuda and Takahashi, eds., Pergamon Press, NY, 1990; 439-441.

Adachi et al., "Unipolar and Bipolar Diffusion Charging of Ultrafine Aerosol Particles," *J. Aerosol Sci.*, 1985; 16(2):109-123.

Büuscher et al., "Performance of a unipolar 'square wave' diffusion charger with variable nt-product," *J. Aerosol Sci.*, 1994; 25(4) 651-663.

Chen et al., "Design and Evaluation of a Nanometer Aerosol Differential Mobility Analyzer (Nano-DMA)," *J. Aerosol Sci.*, 1998; 29(5/6):497-509.

Chen et al., "Electrospraying of Conducting Liquids for Monodisperse Aerosol Generation in the 4 nm to 1.8μm Diameter Range," *J. Aerosol Sci.*, 1995; 26(6):963-977.

Chen et al., "Experimental Investigation of Scaling Laws for Electrospraying: Dielectric Constant Effect," *Aerosol Science and Technology*, 1997; 27(3):367-380.

Fuchs, "On the Stationary Charge Distribution on Aerosol Particles in a Bipolar Ionic Atmosphere," *Geodis:Pura. Appl.*, 1963; 56:185-193.

Ganan-Calvo, "Generation of Steady Liquid Microthreads and Micron-Sized Monodisperse Sprays in Gas Streams," *Phys. Rev. Lett.*, 1998; 80(2):285-288.

Ganan-Calvo, "New Microfluidic Technologies to Generate Respirable Aerosols for Medical Application," *J. of Aerosol Sci.*, 1999; 30(Suppl. 1):S541-S542.

Hoppel et al., "The Nonequililbrium Character of the Aerosol Charge Distribution Produced by Neutralizers," *Aerosol Sci. & Technol.*, 1990; 12:471-496.

Lui et al., "On unipolar diffsion charging of aerosol particles in the continuum regime," *J. Colloid Interface Sci.*, 1977; 58:142-149.

"Minnesota Nanotechnology Summit: Opportunities and Challenges," final program, Mar. 17, 2000, Minneapolis, MN.

Product Literature, BINKS Electrostatic spray painting equipment, 7 pgs, No Date Provided.

Pui et al., "Nanometer Particles: A New Frontier For Multidisciplinary Research," *J. Aerosol Sci.*, 1997; 28(4) 539-544.

Pui et al., "Unipolar Diffusion Charging Ultrafine Aerosols," *Aerosol Sci. Techn.*, 1988; 8:173-187.

Romay et al., "Free electron charging of ultrafine aerosol particles," *J. Aerosol Sci.*, 1992; 23(7):679-692.

Romay et al., "On the combination coefficient of positive ions with ultrafine neutral particles in the transition and free-molecule regimes," *Aerosol Sci. Techn.*, 1992; 17:134-147.

Romay et al., "Unipolar Diffusion Charging of Aerosol Particles at Low Pressure," *Aerosol Sci. Techn.*, 1991; 15:60-68.

Rulison et al., "Scale-up of electrospray atomization using linear arrays of Taylor cones," *Rev. of Sci. Instrum.*, American Institute of Physics, New York, 1993; 64(3):683-686.

Songstad et al, "Advances in alternative DNA delivery techniques," *Plant Cell, Tissue and Organ Culture*, 1995; 40:1-15.

Wiedensohler et al., "A novel unipolar charger for ultrafine aerosol particles with minimal particles losses," *J. Aerosol Sci.*, 1994; 25(4):639-650.

www.crititech.com/technology. Website dated Jun. 5, 2002, 5 pages.

International Application Serial No. PCT/US2007/002718, International Preliminary Report on Patentability, mailed Aug. 14, 2008, 12 pgs.

International Application Serial No. PCT/US2008/001410, Search Report, mailed Nov. 7, 2008.

International Application Serial No. PCT/US2008/001410, Written Opinion, mailed Nov. 7, 2008.

PCT Application No. PCT/US2007/00270 International Search Report, mailed Aug. 24, 2007, 4 pgs.

PCT Application No. PCT/US2007/00270 International Search Written Opinion, mailed Aug. 24, 2007, 7 pgs.

Hamamatsu Photonics K.K., "Small Dots, Fine Patterning," URL http://www.hamamatsu.com Data Sheet. (More information at http://jp.hamamatsu.com/en/rd/pugblication.

* cited by examiner

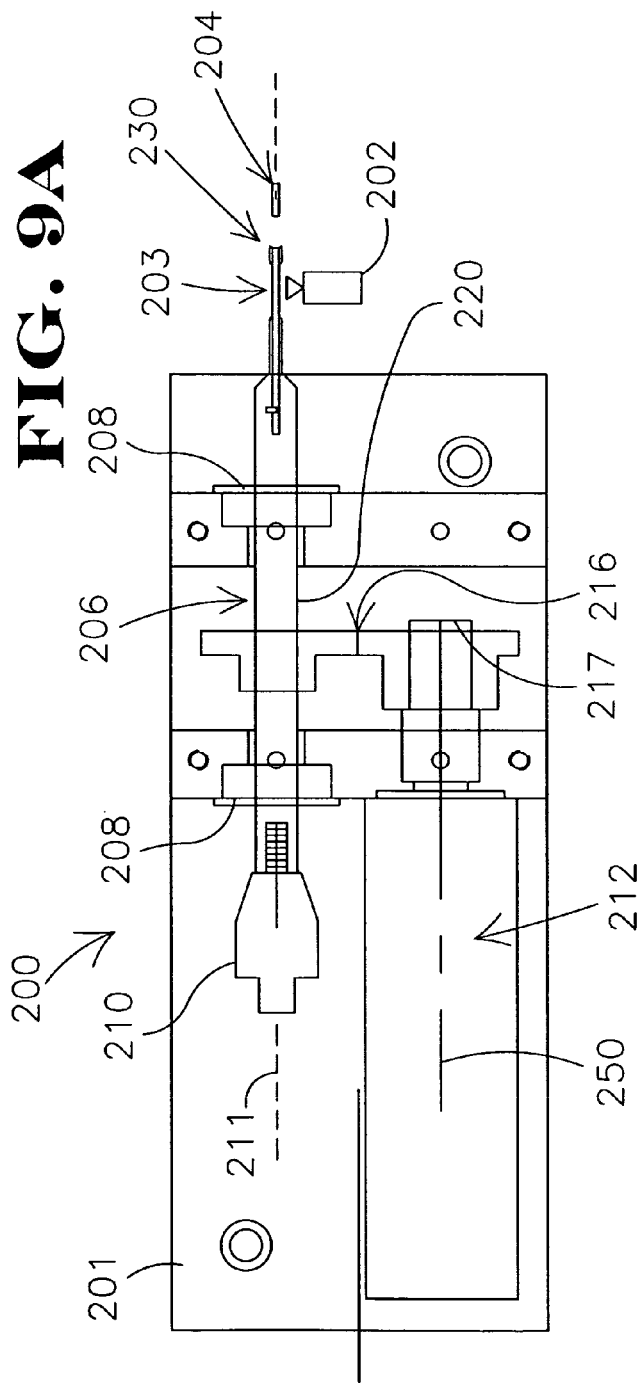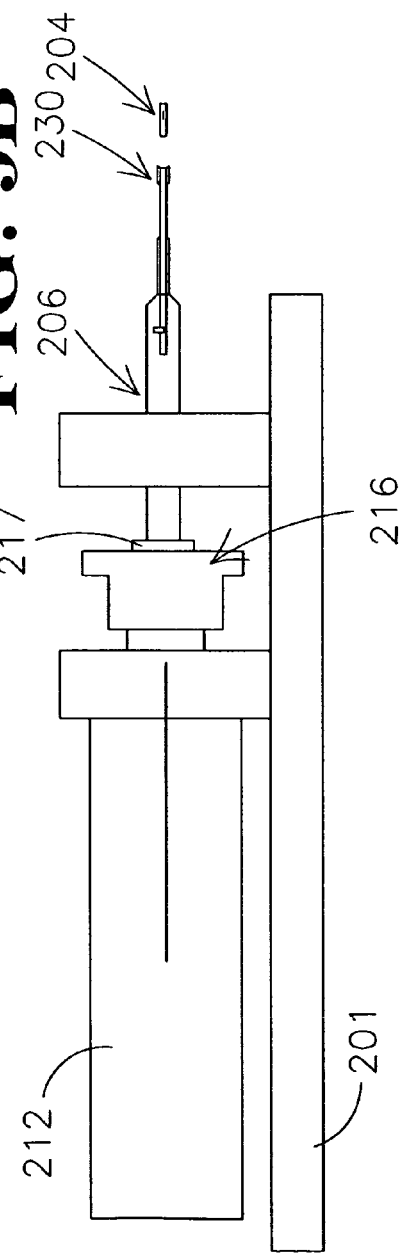

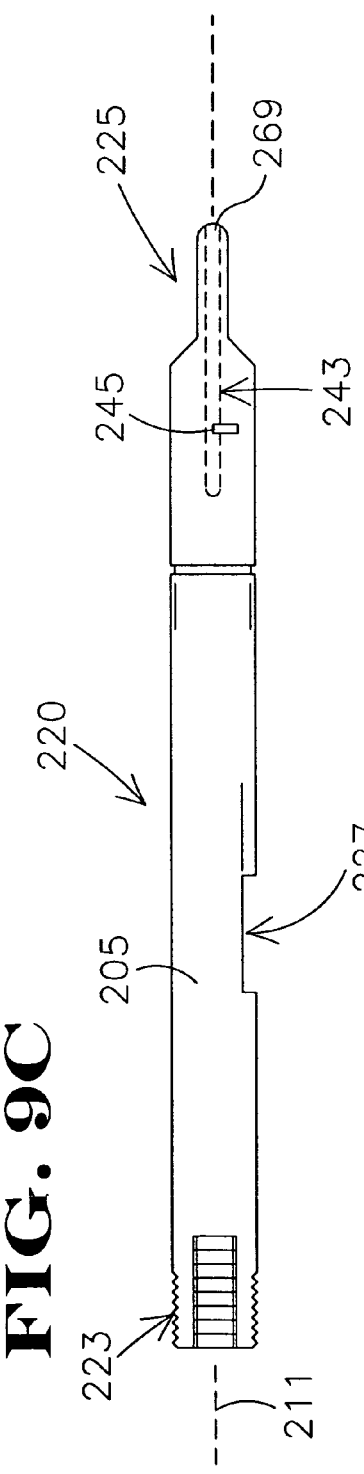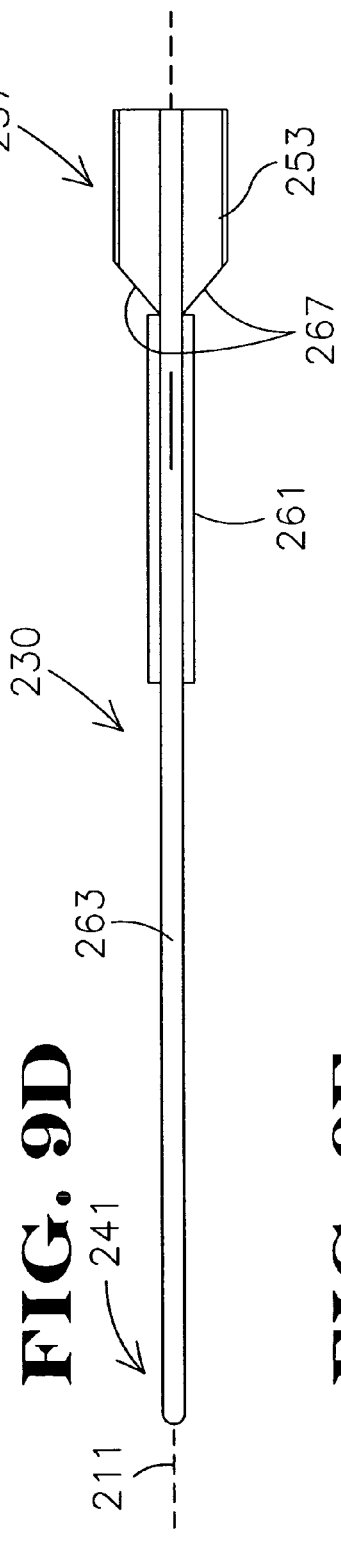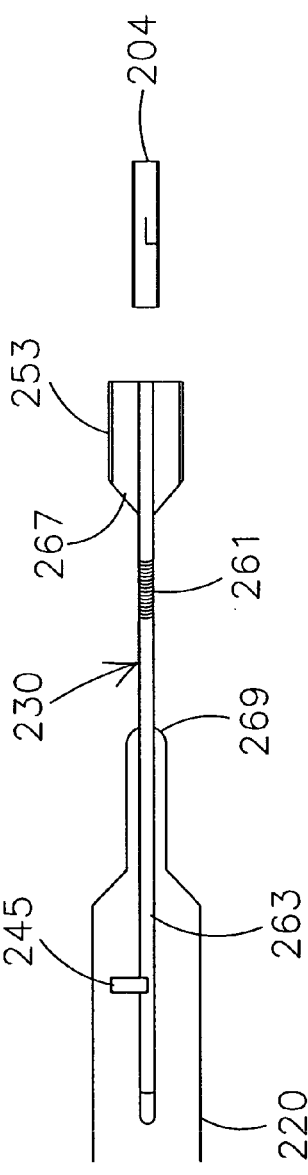

COATING MEDICAL DEVICES

CROSS REFERENCE TO RELATED APPLICATIONS

This is a divisional application of 10/301,473 filed on Nov. 21, 2002 now U.S. Pat. No. 7,247,338, issued Jul. 24, 2007, which is a continuation-in-part of 09/858,865 filed May 16, 2001 now U.S. Pat. No. 6,764,720, issued Jul. 20, 2004 entitled "High Mass Throughput Particle Generation Using Multiple Nozzle Spraying," all of which are incorporated herein by reference.

BACKGROUND OF THE INVENTION

The present invention relates to coating medical devices, and more particularly, the present invention relates to coating medical devices using processes such as electrospray, thermophoretic effect, etc.

It is often beneficial to coat medical devices so that the surfaces of such devices have desired properties or provide desired effects. For example, it is useful to coat medical devices to provide for the localized delivery of therapeutic agents to target locations within the body, such as to treat localized disease (e.g., heart disease) or occluded body lumens. Local drug delivery may be achieved, for example, by coating balloon catheters, stents, and the like with therapeutic agent to be locally delivered. The coating of medical devices may provide for controlled release, which includes long-term or sustained release, of a bioactive material.

Aside from facilitating localized drug delivery, medical devices are coated with materials to provide beneficial surface properties. For example, medical devices are often coated with radiopaque materials to allow for fluoroscopic visualization during placement in the body. It is also useful to coat certain devices to achieve enhanced biocompatibility and to improve surface properties such as lubriciousness.

As indicated herein, it is often beneficial to coat stents, e.g., for the controlled release of pharmacological agents, surface property control and effects, etc. Stents are implanted within vessels in an effort to maintain the patency thereof by preventing collapse and/or impeding restenosis. For example, implantation of a stent may be accomplished by mounting the stent on the expandable portion of a balloon catheter, maneuvering the catheter through the vasculature so as to position the stent at the treatment site within the body lumen, and inflating the balloon to expand the stent so as to engage the lumen wall. The stent deforms in the expanded configuration allowing the balloon to be deflated and the catheter removed to complete the implantation procedure. Further, for example, the use of self-expanding stents obviates the need for a balloon delivery device. Instead, a constraining sheath that is initially fitted above the stent is simply retracted once the stent is in position adjacent the treatment site. Stents and stent delivery catheters are well known in the art and the various configurations thereof makes it impossible to describe each and every stent structure or related materials.

The success of a stent placement can be assessed by evaluating a number of factors, such as thrombosis, neointimal hyperplasia, smooth muscle cell migration, and proliferation following implantation of the stent, injury to the artery wall, overall loss of lumenal patency, stent diameter in vivo, thickness of the stent, and leukocyte adhesion to the lumenal lining of stented arteries. The chief areas of concern are early sub-acute thrombosis and eventual restenosis of the blood vessel due to intimal hyperplasia.

Therapeutic pharmacological agents have been developed to address some of the concerns associated with the placement of the stent. It is often desirable to provide localized pharmacological treatment of the vessel at the site being supported by the stent. As it would be convenient to utilize the implanted stent for such purpose, the stent may serve both as a support for a lumenal wall as well as a delivery vehicle for the pharmacological agent.

Conventionally, coatings have been applied to medical devices, including stents, by processes such as dipping, spraying, vapor deposition, plasma polymerization, as wells as electroplating and electrostatic deposition. Although many of these processes have been used to produce satisfactory coatings, there are numerous potential drawbacks associated therewith.

For example, it is often difficult to achieve coatings of uniform thicknesses, both on the individual parts and on batches of parts. Also, many coating materials are otherwise difficult to use, such as those that are incompatible, insoluble, unsuspendable, or that are unstable coating solutions.

Further, for example, many coating processes result in coatings that do not provide a uniform drug dose per medical device. Further, such conventional methods have generally failed to provide a quick, easy, and inexpensive way of providing drugs onto a stent. For example, deficiencies of such conventional methods are, at least in part, related the control of the coating process (e.g., the ability to control the coating uniformity and thickness, the ability to control the size of particles used to coat the device, the control of the coating so as to control the rate of the release of the drug upon implantation of the stent, etc.). Likewise, in many processes, the coating materials are fairly costly, and in many coating processes such coating materials are wasted due to the type of coating methods being used.

Therefore, the need for an effective method and system of coating medical devices exists (e.g., one that results in a uniform coating on the medical device, such as a stent structure).

SUMMARY OF THE INVENTION

The methods and systems according to the present invention provide for the coating of medical devices (e.g., stents, catheters, etc.). The present invention is particularly beneficial for use in coating stent structures.

A method of coating at least a portion of a medical device according to the present invention includes providing a medical device in a defined volume. The medical device includes at least one surface to be coated. The method further includes providing a plurality of monodisperse coating particles in the defined volume. The plurality of monodisperse coating particles have a nominal diameter of less than 10 micrometers and a geometrical standard deviation of less than 1.2. A plurality of the coating particles are moved towards the at least one surface of the medical device to form a coating thereon.

Another method of coating at least a portion of a medical device according to the present invention includes providing a medical device in a defined volume (e.g., the medical device including at least one surface to be coated) and providing one or more nozzle structures, wherein each nozzle structure includes at least one opening terminating at a dispensing end. A plurality of coating particles are provided in the defined volume by dispensing a plurality of microdroplets having an electrical charge associated therewith from the dispensing ends of the one or more nozzle structures using a nonuniform electrical field created between the dispensing ends and the medical device. Each of the microdroplets includes at least a particle and the electrical charge is concentrated on the particle as the microdroplet evaporates. The method further includes moving the plurality of coating particles towards the medical device to form a coating on the at least one surface of the medical device using the nonuniform electrical field created between the dispensing ends from which the plurality of coating particles is established and the medical device.

A method of coating a stent structure is also described herein. The method includes providing a stent structure in a defined volume along a stent axis, wherein the stent structure includes at least an interior surface adjacent a defined interior volume and at least an exterior surface. At least a portion of the interior surface of the stent structure adjacent the defined interior volume is coated using at least a plurality of first coating particles (e.g., anti-coagulant particles) and at least a portion of the exterior surface of the stent structure is coated using at least a plurality of second coating particles (e.g., anti-inflammatory particles), wherein the plurality of first coating particles is different than the plurality of second coating particles.

The methods described above may also include one or more of the following features: providing an electrical charge on the plurality of monodisperse coating particles; moving a plurality of monodisperse coating particles towards a medical device using an electrical field; providing a plurality of monodisperse coating particles by dispensing a spray of microdroplets having an electrical charge associated therewith, wherein each of the microdroplets includes a particle and wherein the electrical charge is concentrated on the particle as the microdroplet evaporates; an electrical charge of a microdroplet concentrated on the particle that is greater than about 30 percent of the Rayleigh charge limit for the microdroplet; providing a plurality of monodisperse coating particles by dispensing a spray of microdroplets having an electrical charge associated therewith, wherein the electrical charge is concentrated on the particle as the microdroplet evaporates and further wherein, prior to contact with the at least one surface of the medical device, a residual particle volume occupied by the evaporated microdroplet includes less than about 20 percent of a solvent component of the microdroplet; creating an electrical field between an electrode and the medical device after the monodisperse coating particles are provided in the defined volume; providing a plurality of monodisperse coating particles using one or more nozzle structures, wherein each nozzle structure includes at least one opening terminating at a dispensing end thereof from which a plurality of monodisperse coating particles having an electrical charge applied thereto is dispensed; dispensing a plurality of monodisperse coating particles from each of a plurality of nozzle structures by creating a nonuniform electrical field between the dispensing ends of the nozzle structures from which a plurality of monodisperse coating particles are dispensed and a medical device; moving a plurality of monodisperse coating particles towards at least one surface of a medical device to form a coating thereon using a nonuniform electrical field created between dispensing ends from which the plurality of monodisperse coating particles are dispensed and a medical device; providing a medical device that includes a structure defining an interior volume, wherein the structure comprises at least an interior surface adjacent the interior volume and at least an exterior surface that is not adjacent to the interior volume; providing at least one nozzle structure having at least one opening at the dispensing end thereof located within the interior volume defined by a structure and dispensing a plurality of monodisperse coating particles from the at least one nozzle structure with use of a nonuniform electrical field created between the dispensing end of the at least one nozzle and the medical device; providing at least one nozzle structure that includes a capillary tube comprised of a body portion and a tapered capillary tip at the dispensing end of the capillary tube; providing a medical device in a fixed position within a defined volume during the coating process; and providing a medical device that is movable within a defined volume during the coating process.

The method may further include one or more of the additional following features: providing a stent structure defined along a stent axis, wherein the stent structure includes at least an interior surface adjacent a defined interior volume and at least an exterior surface that is not adjacent to the defined interior volume; providing one or more nozzle structures, wherein each nozzle structure includes at least one opening terminating at a dispensing end thereof from which a plurality of monodisperse coating particles having an electrical charge applied thereto is dispensed; adjusting the strength of a nonuniform electrical field to prevent particles from reaching an interior surface of a stent structure; dispensing a plurality of monodisperse coating particles from at least one nozzle structure using a nonuniform electrical field created between a dispensing end thereof and a stent structure; moving a plurality of monodisperse coating particles towards at least one surface of a medical device using a thermophoretic effect; positioning a stent structure such that the stent axis coincides with an axis of an elongated element located within the interior volume of the stent structure and holding the elongated element at a lower temperature than the temperature in the defined volume adjacent the exterior surface of the stent structure such that thermophoretic effect moves the coating particles towards the at least one surface of the stent structure; rotating a stent structure about a stent axis during the coating process; moving a stent structure linearly along a stent axis; controlling the amount of monodisperse coating particles provided into a defined volume; providing a plurality of coating particles that have a nominal diameter of greater than about 1 nanometer and less than about 100 nanometers, that include at least one biologically active ingredient or a coated biologically active ingredient, and/or that include at least one of DNA or coated DNA; providing a plurality of coating particles in a defined volume have a nominal diameter of less than 10 micrometers and a geometrical standard deviation of less than 1.2; and providing one or more nozzle structures that each include at least a first and second opening terminating at the dispensing end of each nozzle structure (e.g., for dispensing coated particles, dispensing hard to spray particles, dispensing particles that define voids therewithin, etc.).

The methods described herein, preferably those used to coat stent structures, may include one or more of the following features: providing an elongated cylindrical body member defining an interior volume thereof along an axis, positioning the stent structure along the axis of the elongated cylindrical body member, and positioning a plurality of nozzle structures radially about the axis of the elongated cylindrical body member and linearly along the elongated cylindrical body member in the direction of the axis thereof; providing nozzle structures that each include a capillary tube comprised of a body portion and a tapered capillary tip at the dispensing end of the capillary tube; providing nozzles structures that each include a tapered portion used to define an opening, and wherein at least a part of each of the plurality of the nozzle structures extend from an integral conductive portion associated with the body member; providing a plurality of the nozzle structures that each include a solid post along a center axis extending through an opening at the dispensing end; providing one or more nozzle structures that may include an elongated radial opening in the body member and/or an elongated opening in the body member lying parallel to the axis thereof; positioning a stent structure such that the stent axis coincides with an axis of an elongated element and using spacing elements to maintain a distance between the stent structure and the elongated element; positioning a stent structure such that the stent axis coincides with an axis of an elongated element, wherein the elongated element is sized based on the defined interior volume of the stent structure such that a surface of the elongated element is in direct contact with the interior surface of the stent structure; removing an elongated element from the interior volume of the stent structure after a plurality of coating particles are moved towards the exterior surface of the stent structure to form a coating thereon; providing a stent structure that includes an open framework including stent material lying radially from the stent axis and a configuration of openings separating portions of the stent material; providing an elongated element sized to stretch the stent structure from a normal state; removing an elongated element from an interior volume of a stent structure after a plurality of coating particles are moved towards the exterior surface of the stent structure resulting in a sheath over the open framework thereof including openings separating portions of stent material; providing a conductive elongated element along the axis of the stent structure, wherein the stent structure and the conductive elongated element are spaced a distance apart, and creating an electric field between the conductive elongated element and the stent structure that is opposite a nonuniform electric field created between dispensing ends of nozzle structures and the stent structure; providing an elongated element along the axis of the stent structure, wherein the stent structure and the conductive elongated element are spaced a distance apart, and using the elongated element to provide a gas stream within the defined interior volume of the stent structure; and moving a plurality of coating particles towards the at least one surface of the medical device to form a coating thereon while the stent structure is in a vertical position such that the stent does not sag along its stent axis.

A system for use in coating at least one surface of a medical device according to the present invention includes a particle source, a holding fixture operable to position a medical device in a defined volume; and a dispensing device configured to receive source material from the particle source and dispense a plurality of monodisperse coating particles into the defined volume. The dispensing device includes one or more nozzle structures, wherein each nozzle structure includes at least one opening terminating at a dispensing end thereof from which a plurality of monodisperse coating particles having an electrical charge applied thereto is dispensed. The system further includes an electrode structure that includes an electrode isolated from the dispensing ends of the one or more nozzle structures, wherein the electrode structure is operable to create a nonuniform electrical field between the dispensing ends of the one or more nozzle structures and the medical device for use in providing the plurality of monodisperse coating particles in the defined volume. The plurality of monodisperse coating particles have a nominal diameter of less than 10 micrometers and a geometrical standard deviation of less than 1.2. Further, the nonuniform electric field is operable to assist in moving a plurality of the coating particles towards the at least one surface of the medical device to form a coating thereon.

Another system for use in coating at least one surface of a stent structure according to the present invention includes a particle source and a holding fixture operable to position a stent structure defined along a stent axis in a defined volume, wherein the stent structure includes at least an interior surface adjacent a defined interior volume and at least an exterior surface. The system further includes a dispensing device configured to receive source material from the particle source and dispense a plurality of microdroplets having an electrical charge associated therewith from the dispensing ends of the one or more nozzle structures into the defined volume, wherein each of the microdroplets includes at least a particle, and further wherein the electrical charge is concentrated on the particles as the microdroplets evaporate resulting in a plurality of coating particles. Yet further, the system includes an electrode structure that includes an electrode isolated from the dispensing ends of the one or more nozzle structures. The electrode structure is operable to create a nonuniform electrical field between the dispensing ends of the one or more nozzle structures and the stent structure for use in providing the plurality of coating particles in the defined volume and moving the plurality of coating particles towards the stent structure to form a coating on the at least one surface thereof.

The systems described herein may also include one or more of the following features: an electrode structure that includes a grounded medical device; an electrode structure that includes a ring electrode positioned forward of one or more nozzle structures; a dispensing device configured to dispense a spray of microdroplets having an electrical charge associated therewith, wherein the electrical charge of the microdroplet concentrated upon evaporation on the particle is greater than about 30 percent of the Rayleigh charge limit for the microdroplet; a dispensing device configured such that, prior to contact with the at least one surface of a medical device, a residual particle volume occupied by an evaporated microdroplet includes less than about 20 percent of a solvent component of the originally dispensed microdroplet; a holding fixture operable to position a medical device such that at least one nozzle structure of the dispensing device is operable within the interior volume defined by a medical device structure; an electrode structure operable to create a nonuniform electrical field between the dispensing end of the at least one nozzle structure and a medical device for use in providing the plurality of monodisperse coating particles in the interior volume of the medical device; an elongated element sized to be positioned or moved into the defined interior volume of a medical device; a dispensing device that includes a plurality of nozzle structures; a holding fixture configured to hold the medical device in a fixed position within the defined volume; a holding fixture configured for movement of the medical device within the defined volume; a holding fixture configured to receive a stent structure, wherein the stent structure is defined along a stent axis and includes at least an interior surface adjacent a defined interior volume and at least an exterior surface; a holding fixture configured to at least rotate the stent structure about the stent axis; a holding fixture configured to at least move the stent structure linearly along the stent axis; a control system operable to control the amount of monodisperse coating particles provided into a defined volume; a control system operable to adjust the strength of the nonuniform electrical field; and a particle source that includes source material for use in providing a plurality of coating particles, wherein the source material includes at least one biologically active ingredient or at least one coated biologically active ingredient.

The systems described herein for coating a medical device may also include a holding fixture that includes an elongated substantially non-conductive tube for receiving the stent structure thereon and an elongated conductive element. At least a portion of the elongated conductive element extends through the elongated substantially non-conductive tube, and further wherein the elongated conductive element comprises a conductive contact section. A compression apparatus is configured to provide for expansion of the elongated substantially non-conductive tube such that an exterior surface thereof is in contact with at least a portion of the interior surface of the stent structure and such that a portion of the stent structure is in electrical contact with the conductive contact section.

The systems described herein for coating a medical device may also include one or more of the following features: a dispensing device that includes an elongated cylindrical body member defining an interior volume thereof along an axis, wherein the holding fixture is operable to position the stent structure along the axis of the elongated cylindrical body member, and further wherein the one or more nozzle structures are positioned radially about the axis of the elongated cylindrical body member and linearly along the elongated cylindrical body member in the direction of the axis thereof; a plurality of nozzle structures that each include a capillary tube comprised of a body portion and a tapered capillary tip at the dispensing end of the capillary tube; a plurality of the nozzle structures that each include a tapered portion used to define an opening, wherein at least a part of each of the plurality of the nozzle structures extend from an integral conductive portion associated with the body member; a plurality of the nozzle structures that each include a solid post along a center axis extending through an opening at the dispensing end; a plurality of the nozzle structures that include an elongated radial opening in a body member; a plurality of the nozzle structures that include an elongated opening in the body member lying parallel to an axis thereof; an elongated element extending along an axis coinciding with the axis of a stent structure and spacing elements operable to maintain a distance between the stent structure and the elongated element; a holding fixture that includes an elongated element sized based on the defined interior volume of the stent structure such that a surface of the elongated element is in direct contact with the interior surface of the stent structure; a power source configured to create an electric field between a conductive elongated element and a stent structure that is opposite a nonuniform electric field created between dispensing ends of nozzle structures and the stent structure; and an elongated element configured to provide a gas stream within the defined interior volume of a stent structure.

Yet another system for use in coating at least one surface of a medical device includes a particle generation apparatus operable to provide a plurality of coating particles in a defined volume and a holding fixture operable to position a stent structure defined along a stent axis in the defined volume. The stent structure includes at least an interior surface adjacent an interior volume and an exterior surface. The holding fixture includes an elongated element located within the interior volume of the stent structure. The system further includes a temperature control apparatus operable to hold the elongated element at a lower temperature than the temperature in the defined volume adjacent the exterior surface of the stent structure such that thermophoretic effect moves the coating particles towards the at least one surface of the stent structure.

BRIEF DESCRIPTION OF THE DRAWINGS

FIGS. 9A-9E are a top view, a side view, and three additional more detailed views of portions shown in the top and side views, respectively. The figures show a holding fixture that may be employed in the medical device coating system shown generally in FIG. 1 according to the present invention; particularly, the holding structure is beneficial in holding a stent structure to be coated.

FIG. 13A is a perspective view of the medical device coating system. FIG. 13B is a cross-section view of a portion of the medical device coating system shown in FIG. 13A. FIG. 13C is a more detailed view of a technique used during the coating process involving either electric field forces and/or mechanical forces such as those provided by air streams.

DETAILED DESCRIPTION OF THE EMBODIMENTS

The present invention shall generally be described with reference to FIG. 1. Various embodiments of the present invention shall then be described with reference to FIGS. 2-16. It will become apparent to one skilled in the art that elements from one embodiment may be used in combination with elements of the other embodiments, and that the present invention is not limited to the specific embodiments described herein but only as described in the accompanying claims. For example, one or more different nozzle structures may be used for providing particles used in the coating methods and systems.

The present invention provides for coated devices (e.g., coated stent structures) and also systems and methods for coating objects, such as medical devices. With use of the present invention, for example, coatings having uniform properties can be accomplished. Further, the present invention provides for the efficient and cost effective use of coating materials.

The present invention is directed to coating systems and methods that employ the generation of particles, such as, for example, nanoparticles, for use in coating objects. The present invention is particularly advantageous in the coating of medical devices (e.g., coating such devices with DNA, RNA, coated DNA particles, etc. As further described below, the systems and methods according to the present invention may use one or more single nozzle electrospray apparatus such as that previously described in U.S. Pat. No. 6,093,557 to Pui, et al., entitled "Electrospraying Apparatus and Method for Introducing Material into Cells," issued 25 Jul. 2000 (e.g., single and dual capillary configurations), and also described in the papers entitled, "Electrospraying of Conducting Liquids for Dispersed Aerosol Generation in the 4 nm to 1.8 μm Diameter Range" by Chen, et al., *J. Aerosol Sci.,* Vol. 26, No. 6, pp. 963-977 (1995), and entitled "Experimental Investigation of Scaling Laws for Electrospraying: Dielectric Constant Effect" by Chen, et al., *Aerosol Science and Technology,* 27:367-380 (1997), or may use a multiple nozzle structure electrospray apparatus such as described in U.S. Patent Application US-2002-0007869-A1, entitled "High Mass Throughput Particle Generation Using Multiple Nozzle Spraying," published on 24 Jan. 2002, which are all hereby incorporated in their entirety by reference thereto. Further, other apparatus for generating particles, such as, for example, those described with reference to FIGS. 8A and 8B, may also be employed in one or more embodiments described herein.

Figure 1:
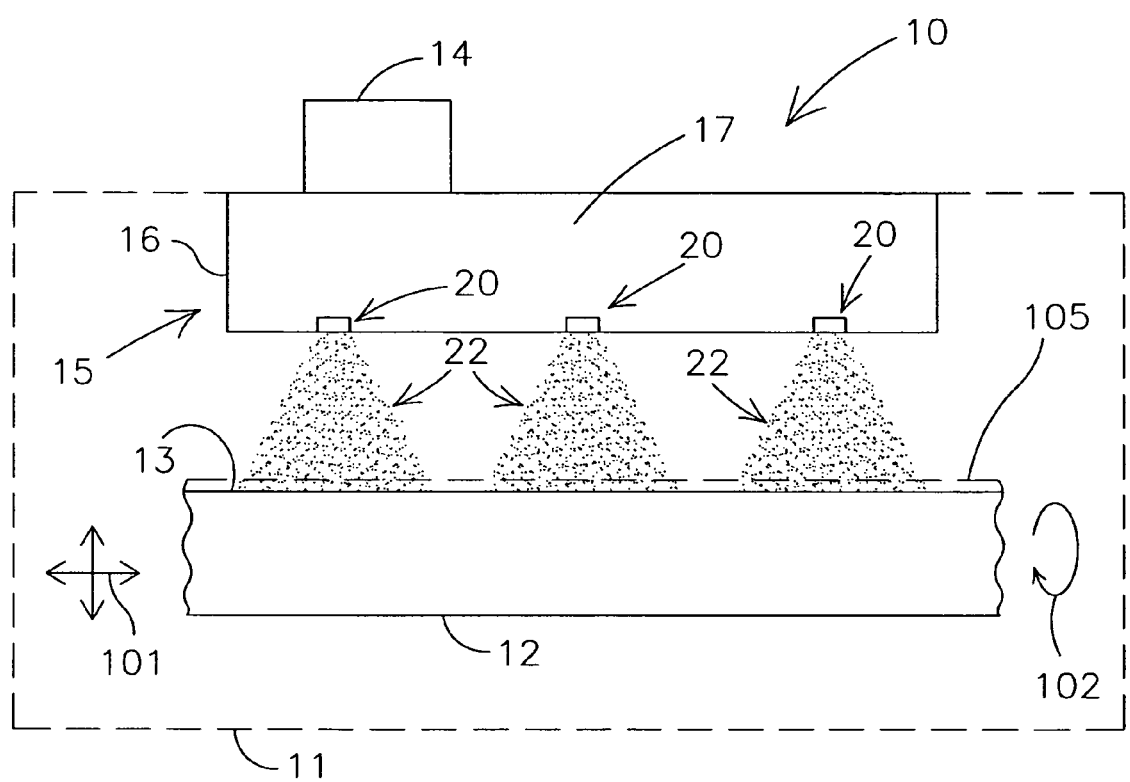
FIG. 1 is a general diagram illustrative of a medical device coating system, e.g., a nanoparticle generator system using electrospray techniques for coating surfaces, in accordance with the present invention.

As shown in FIG. 1, the present invention provides a medical device coating system 10 employing a dispensing apparatus 15 to establish one or more sprays of particles 22 (e.g., sprays of microdroplets which evaporate to form sprays of particles). The dispensing apparatus 15 includes one or more nozzle structures 20 which receive source material 17 and establish sprays of particles 22 forward thereof, e.g., in the direction of medical device 12. The particles 22 are moved toward at least one surface 13 of the medical device 12 to form a coating 105 thereon. The medical device 12 is preferably located in a defined volume (shown generally by the dashed line 11) where the particles 22 are provided. The defined volume may, for example, be a reactor chamber, a chamber of a stent coating system, a volume formed by a body member (e.g., as described with reference to FIG. 10), a vacuum chamber, a pressurized and/or heated chamber, a volume of open air space, etc.

The dispensing apparatus 15 further includes a source holding apparatus 16 for providing the source material 17 to the plurality of nozzle structures 20 under control of control mechanism 14, e.g. hardware and/or software control. Each of the one or more nozzle structures 20 is configured to provide a spray of particles 22 to the defined volume 11 where the medical device is located. Generally, for example, in one or more embodiments, such spray of particles 22 established forward of each of the one or more nozzle structures 20.

The source material 17 held in the source holding apparatus 16 may be any source of material which can be provided in the defined volume in particle form as described according to the present invention herein. Preferably, the source material 17 is a fluid composition that may include a solution, a suspension, a microsuspension, an emulsion, a microemulsion, a gel, a hydrosol, or any other fluid-like compositions that when provided according to the present invention results in the generation of particles. For example, such fluid compositions may include a solution of dissolved active ingredients, e.g., drug active ingredients, according to one embodiment of the present invention. However, it is contemplated that the source material may also be a dry material, e.g., material having substantially no solvent or liquid component associated therewith, as well.

As used herein, an active ingredient refers to any component that provides a useful function when provided in particle form, particularly when provided as nanoparticles. The present invention is particularly beneficial for spraying nanoparticles and also is particularly beneficial for spraying particles including biologically active ingredients.

As such, the term "active ingredient" refers to material which is compatible with and has an effect on the substrate or body with which it is used, such as, for example, drug active ingredients, chemical elements for forming nanostructures, and elements for film coatings, e.g., polymers, excipients, etc. The term "biologically active ingredient" or "biologically active material or component" is a subset of active ingredient and refers to material which is compatible with and has an effect (which may, for example, be biological, chemical, or biochemical) on the animal or plant with which it is used and includes, for example, medicants such as medicines, pharmaceutical medicines, and veterinary medicines, vaccines, genetic materials such as polynucleic acids, cellular components, and other therapeutic agents, such as those described below.

As used herein, the term particle, and as such nanoparticle, includes solid, partially solid, and gel-like droplets and microcapsules which incorporate solid, partially solid, gel-like or liquid matter. Particles provided and employed herein may have a nominal diameter as large as 10 micrometers. As used herein, nanoparticle refers to a particle having a nominal diameter of less than 2000 nm. The present invention is particularly beneficial in spraying nanoparticles having a nominal diameter greater than 1 nanometer (nm), and further preferably having a nominal diameter less than 1000 nm, and more preferably less than 100 nm.

Further, the particles used for coating medical devices described herein are preferably monodisperse coating particles. As used herein, monodisperse coating particles are coating particles that have a geometrical standard deviation of less than 1.2. In other words, the standard deviation with respect to mean particle size of particles provided according to the present invention is preferably less than or equal to 20%.

With further reference to FIG. 1, the method of coating at least a portion of a medical device 12 (e.g., surface 13 of medical device 12) shall be described. Generally, the medical device 12 is preferably positioned within the defined volume 11 (e.g., the defined volume 11 indicated generally by the dashed line that may be representative of a chamber or other structure encompassing one or more elements of the medical device coating system 10). With the medical device 12 provided in the defined volume 11, the method of coating at least one surface thereof may be initiated.

A plurality of coating particles 22 are provided in the defined volume 11 (e.g., monodisperse coating particles 22). The coating particles 22 are then moved towards at least one surface 13 of the medical device 12 to form a coating thereon. The coating is represented generally as the dashed layer 105.

Depending upon the method used to move the coating particles 22 towards the at least one surface 13 of the medical device 12, the coating particles 22 may either be charged particles or uncharged particles. For example, if an electric field is used to move the coating particles 22 towards the surface 13 of the medical device 12, then the coating particles 22 are charged particles, preferably, highly charged particles. On the other hand, if a thermophoretic effect is used to move the coating particles towards the surface 13 of the medical device 12, then the coating particles may not need to be charged particles. For example, such uncharged particles may be provided using a dispensing apparatus such as that described with reference to FIGS. 8A and 8B, or, for example, electrosprayed according to the present invention and neutralized.

In different embodiments of the coating method according to the present invention, the coating particles 22 may be provided in the defined volume 11 prior to or simultaneously with the movement of the coating particles 22 towards the surface 13 of the medical device 12. For example, highly charged particles may be provided in the defined volume 11 prior to the establishment of an electric field utilized to move the coating particles 22 towards the surface 13 of the medical device 12. Likewise, as is described herein, for example, an electric field may be established between the medical device 12 and the dispensing apparatus 15 so as to simultaneously produce the particles 22 forward of the dispensing apparatus 15 and move such charged particles 22 towards surface 13 of the medical device 12 (e.g., an electrode may be positioned within an interior volume of the medical device 12 to establish an electric field between the medical device 12 and the dispensing apparatus 15 or the medical device 12 may be grounded to establish such an electric field therebetween).

Further, the medical device 12 and/or the dispensing apparatus 15 (or any component thereof) may be moved in any one or more different directions as represented generally by the horizontal/vertical movement arrows 101 and radial movement arrow 102 prior to, during, or after the coating process for any particular reason. Such movement of the medical device 12 or any elements of the coating system 10 may be performed using any apparatus configured for the desired motion. The present invention is not limited to any particular structure for providing such movement. Further, the present invention is not limited to movement of any elements of the coating system 10 or the medical device 12 during the coating process. In other words, for example, the medical device 12 may remain in a fixed position within the defined volume 11 as the coating process is performed.

As described above, the spray of particles 22 provided from the one or more nozzle structures 20 are moved toward at least one surface 13 of the medical device 12. Such particles 22 are deposited onto the surface 13 for coating purposes. As used herein, coating refers to forming a layer or structure on a surface. The coated layer or structure formed on the surface may be a coating that adheres to an underlying layer or the surface 13, or a coating that does not adhere to the surface or an underlying layer. Any level of adherence to the surface 13 or an underlying layer is contemplated according to the present invention. For example, a coating formed on surface 13 of the medical device 12 may be formed as a sheath about a structure (e.g., a stent structure) without necessarily having adhesion between the layer and the medical device 12.

Likewise, an adhesion layer may be deposited on a medical device 12 prior to forming a coating on the medical device 12 such that greater adhesion is accomplished. The adhesion layer may also be coated on the surface 13 of the medical device 12 employing method and/or systems according to the present invention.

Various embodiments of the coating methods and systems described are suitable to allow one or more medical devices to be coated as a batch. However, the present invention is not limited to only coating medical devices in batches, i.e., coating a group of one or more devices in one batch process followed by coating a second group of one or more devices in a second batch process. The methods and systems of the present invention can be utilized to continuously run medical devices through the systems such that the process does not have to be started and stopped for coating the medical devices in batches. In other words, a plurality of medical devices can be coated through a continuous process.

In one or more of the embodiments of the present invention, single or multiple coating materials can be applied to medical devices, separately or simultaneously. For example, a coating sprayed may include multiple coating materials, different nozzle structures may be provided with different source materials for controlling and spraying different coating materials, different nozzle structures may be controlled for use during different time periods so as to provide different layers of coating materials on at least a portion of the medical device, multiple layers may be sprayed using the same or different source materials (e.g., forming a somewhat laminated coating), the entire medical device or just a portion of the medical device may be coated (e.g., a charge could be applied to a portion of the surface to attract all of or a majority of the sprayed particles to the charged portion), different portions of the medical device may be sprayed with more coating materials than the remainder of the medical device, and/or masking materials may be used to mask certain portions of the medical device from having coating applied thereto.

As indicated above, the present invention contemplates applying one layer or multiple layers of the same or different coating materials. Such, layers may perform identical or different functions (e.g., to provide for biocompatibility, to control drug release, etc.).

The medical devices used in conjunction with the present invention include any device amenable to the coating processes described herein. The medical device, or portion of the medical device, to be coated or surface modified may be made of metal, polymers, ceramics, composites or combinations thereof, and for example, may be coated with one or more of these materials. For example, glass, plastic or ceramic surfaces may be coated. Further, the present invention may be used to form a coating on surfaces of other objects as well, e.g., metal substrates or any other surfaces that may be rendered conductive (e.g., whether flat, curved, or of any other shape).

Although the present invention is described herein with specific reference to a vascular stent, other medical devices within the scope of the present invention include any medical devices such as those, for example, which are used, at least in part, to penetrate and/or be positioned within the body of a patient, such as, but clearly not limited to, those devices that are implanted within the body of a patient by surgical procedures. Examples of such medical devices include implantable devices such as catheters, needle injection catheters, blood clot filters, vascular grafts, stent grafts, biliary stents, colonic stents, bronchial/pulmonary stents, esophageal stents, ureteral stents, aneurysm filling coils and other coiled coil devices, trans myocardial revascularization ("TMR") devices, percutaneous myocardial revascularization ("PMR") devices, lead wires, implantable spheres, pumps, etc., as are known in the art, as well as devices such as hypodermic needles, soft tissue clips, holding devices, and other types of medically useful needles and closures. Any exposed surface of these medical devices may be coated with the methods and systems of the present invention including, for example, the inside exposed surface and the outside exposed surface of a tubular medical device which is open at both ends, e.g., a stent structure.

The coating materials used in conjunction with the present invention are any desired, suitable substances such as defined above with regard to active ingredients and biologically active ingredients. In some embodiments, the coating materials comprise therapeutic agents, applied to the medical devices alone or in combination with solvents in which the therapeutic agents are at least partially soluble or dispersible or emulsified, and/or in combination with polymeric materials as solutions, dispersions, suspensions, lattices, etc. The terms "therapeutic agents" and "drugs", which fall within the biologically active ingredients classification described herein, are used interchangeably and include pharmaceutically active compounds, nucleic acids with and without carrier vectors such as lipids, compacting agents (such as histones), virus, polymers, proteins, and the like, with or without targeting sequences. The coating on the medical devices may provide for controlled release, which includes long-term or sustained release, of a bioactive material.

Specific examples of therapeutic or biologically active ingredients used in conjunction with the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. For example, biologically active solutes include anti-thrombogenic agents such as heparin, heparin derivatives, urokinase, and PPACK (dextrophenylalanine proline arginine chloromethylketone); prostaglandins, prostacyclins/prostacyclin analogs; antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine, its derivatives and salts (e.g., arginine hydrochloride); antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, NO-protein adducts, NO-polysaccharide adducts, polymeric or oligomeric NO adducts or chemical complexes; anticoagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promoters; vascular cell growth inhibitors such as growth factor inhibitors (e.g., PDGF inhibitor Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; Tyrosine kinase inhibitors, chymase inhibitors, e.g., Tranilast, ACE inhibitors, e.g., Enalapril, MMP inhibitors (e.g., Ilomastat, Metastat), GP IIb/IIIa inhibitors (e.g., Intergrilin, abciximab), seratonin antagonist, and 5-HT uptake inhibitors; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof; and beta blockers. These and other compounds may be added to a coating solution, including a coating solution that includes a polymer.

Modifications to or various forms of the coating materials and/or additional coating materials for use in coating a medical device according to the present invention are contemplated herein as would be apparent to one skilled in the art. For example, such coating materials may be provided in derivatized form or as salts of compounds.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include, as a primary example, those proteins or polypeptides that can compensate for defective or deficient species in an animal, or those that act through toxic effects to limit or remove harmful cells from the body. In addition, the polypeptides or proteins that can be incorporated into the polymer coating, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Coating materials other than therapeutic agents include, for example, polymeric materials, sugars, waxes, and fats, applied alone or in combination with therapeutic agents, and monomers that are cross-linked or polymerized. Such coating materials are applied in the form of, for example, powders, solutions, dispersions, suspensions, and/or emulsions of one or more polymers, optionally in aqueous and/or organic solvents and combinations thereof or optionally as liquid melts including no solvents. When used with therapeutic agents, the polymeric materials are optionally applied simultaneously with, or in sequence to (either before or after), the therapeutic agents. Such polymeric materials employed as, for example, primer layers for enhancing subsequent coating applications (e.g., application of alkanethiols or sulfhydryl-group containing coating solutions to gold-plated devices to enhance adhesion of subsequent layers), layers to control the release of therapeutic agents (e.g., barrier diffusion polymers to sustain the release of therapeutic agents, such as hydrophobic polymers; thermal responsive polymers; pH-responsive polymers such as cellulose acetate phthalate or acrylate-based polymers, hydroxypropyl methylcellulose phthalate, and polyvinyl acetate phthalate), protective layers for underlying drug layers (e.g., impermeable sealant polymers such as ethylcellulose), biodegradable layers, biocompatible layers (e.g., layers comprising albumin or heparin as blood compatible biopolymers, with or without other hydrophilic biocompatible materials of synthetic or natural origin such as dextrans, cyclodextrins, polyethylene oxide, and polyvinyl pyrrolidone), layers to facilitate device delivery (e.g., hydrophilic polymers, such as polyvinyl pyrrolidone, polyvinyl alcohol, polyalkylene glycol (i.e., for example, polyethylene glycol), or acrylate-based polymer/copolymer compositions to provide lubricious hydrophilic surfaces), drug matrix layers (i.e., layers that adhere to the medical device and have therapeutic agent incorporated therein or thereon for subsequent release into the body), and epoxies.

When used as a drug matrix layer for localized drug delivery, the polymer coatings may include any material capable of absorbing, adsorbing, entrapping, or otherwise holding the therapeutic agent to be delivered. The material is, for example, hydrophilic, hydrophobic, and/or biodegradable, and is preferably selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyurea, polyacrylate, polyacrylic acid and copolymers, polyorthoesters, polyanhydrides such as maleic anhydride, polycarbonates, polyethylene, polypropylenes, polylatic acids, polystyrene, natural and synthetic rubbers and elastomers such as polyisobutylene, polyisoprene, polybutadiene, including elastomeric copolymers, such as Kraton®, styrene-isobutylene-styrene (SIBS) copolymers; polyglycolic acids, polycaprolactones, polyhydroxybutyrate valerates, polyacrylamides, polyethers, polysaccharides such as cellulose, starch, dextran and alginates; polypeptides and proteins including gelatin, collagen, albumin, fibrin; copolymers of vinyl monomers such as ethylene vinyl acetate (EVA), polyvinyl ethers, polyvinyl aromatics; other materials such as cyclodextrins, hyaluronic acid and phosphoryl-cholines; and mixtures and copolymers thereof. Coatings from polymer dispersions such as polyurethane dispersions (BAYHDROL, etc.) and acrylic latex dispersions are also within the scope of the present invention. Preferred polymers include polyurethanes; polyacrylic acid as described in U.S. Pat. No. 5,091,205; and aqueous coating compositions comprising an aqueous dispersion or emulsion of a polymer having organic acid functional groups and a poly-functional crosslinking agent having functional groups capable of reacting with organic acid groups, as described in U.S. Pat. No. 5,702,754.

The release rate of drugs from drug matrix layers is largely controlled, for example, by variations in the polymer structure and formulation, the diffusion coefficient of the matrix, the solvent composition, the ratio of drug to polymer, potential chemical reactions and interactions between drug and polymer, the thickness of the drug adhesion layers and any barrier layers, and the process parameters, e.g., drying, etc. The coating(s) applied by the methods and apparatuses of the present invention may allow for a controlled release rate of a coating substance with the controlled release rate including both long-term and/or sustained release.

The coating material may include suspended particles, e.g., a powder. For example, the suspension particles may be fused to the surface of the medical device by an adhesion coating or some other technique such as electrostatic phenomena.

The coatings of the present invention are applied such that they result in a suitable thickness, depending on the coating material and the purpose for which the coating or coatings are applied. For example, coatings applied for localized drug delivery are typically applied to a thickness of at least about 1 micron and not greater than 30 microns. Preferably, the thickness is greater than 2 microns. Further, preferably, the thickness is not greater than 20 microns. In addition, very thin coatings such as those as thin as 100 Angstroms may be provided. Much thicker coatings of more than 30 microns are also possible.

Figure 2:
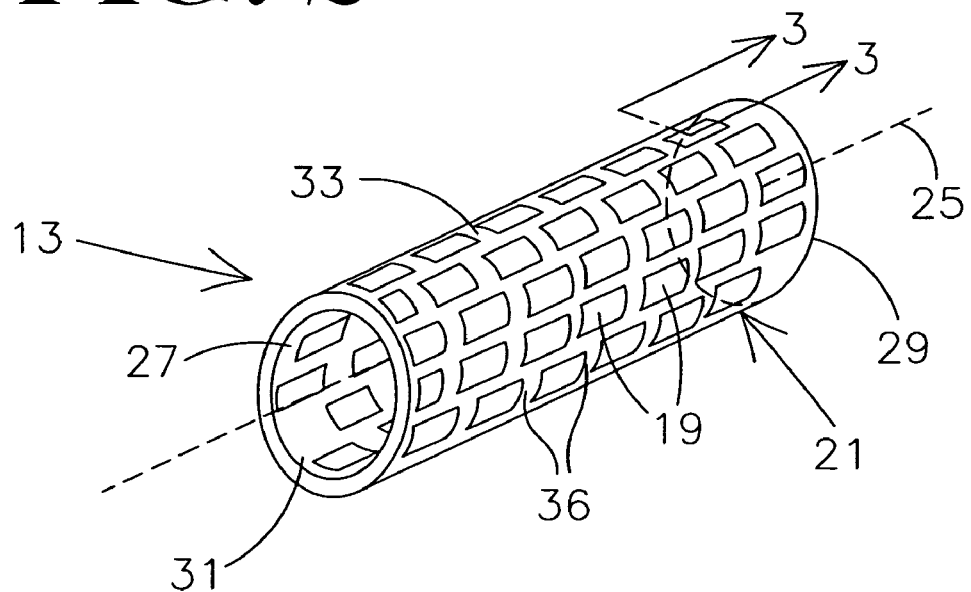
FIG. 2 is a general diagram of an illustrative embodiment of a stent structure that can be coated according to the present invention.

Preferably, according to the present invention, the medical device 12 is a stent structure. FIG. 2 shows one illustrative exemplary embodiment of a stent structure 13. Stent structure 13 includes generally a cylindrical body of open framework material 21 extending along an axis 25. In other words, the material forming the stent structure 13 has openings 19 defined between portions of stent material 36 forming the structure 13. Such open framework of material 21 is shown generally in FIG. 2 and only indicates that typical stent structures include stent material and openings which form the structure. The present invention is not limited to any particular stent construction. Generally, the stent structure 13 extends along the axis 25 from a first open end 27 to a second open end 29. The stent structure 13 generally includes an exterior surface 33 of the stent material 36 which generally faces opposite an interior surface 31 of the stent structure 13 which defines an interior volume between the first open end 27 and second open end 29 thereof.

Figure 3:
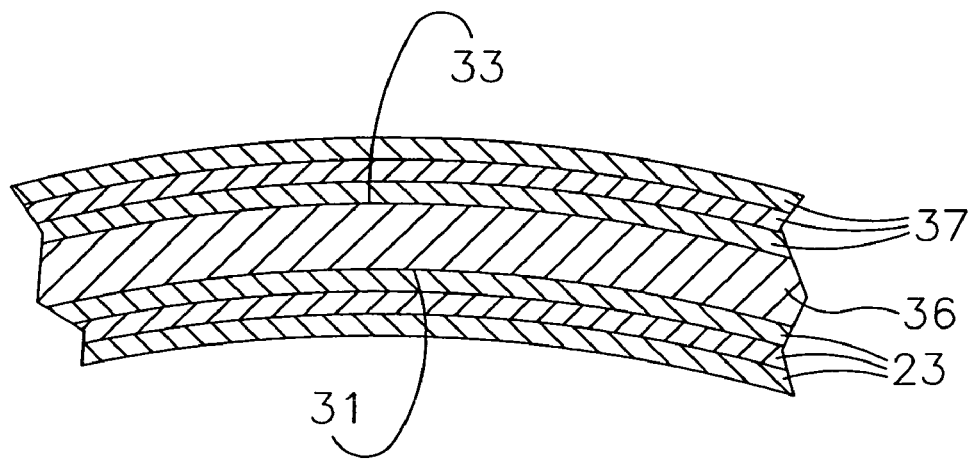
FIG. 3 is a detailed portion of the stent structure of FIG. 2 coated according to one or more embodiments of the present invention.

FIG. 3 generally shows an illustrative diagram of a portion of the stent structure 13 of FIG. 2 as coated using the present invention. For example, the exterior surface 33 of the stent structure 13 may be coated with one or more layers 37. Likewise, the interior surface 31 adjacent the interior volume of the stent structure 13 may be coated with one or more coatings 23. For example, the exterior surface 33 may be coated with an adhesion layer and one or more therapeutic agents. For example, an anti-inflammatory therapeutic agent may be the final layer formed on the exterior surface of the stent structure 13.

Further, for example, one or more layers 23 may be formed on the interior surface 31 and may include, for example, an adhesion layer adjacent surface 31 with the final coating being in the form of an anti-coagulant biologically active ingredient.

One skilled in the art will recognize that FIGS. 2 and 3 are but one illustrative and diagrammatical example of a stent structure that may be coated according to the present invention. The variety of different stent structures are numerous and coating of any and all such structures is contemplated according to the present invention (e.g., self expanding structures, structures formed of material not in the form of open framework material, etc.). Further, it is also only illustrative of the number of layers that may be coated on any one surface of the stent structure 13. For example, the actual coating applied by the present invention may take the form of a multi-layered laminate-type structure that is adherent to one or more surfaces of the stent structure 13 without any adhesion layer.

With further reference to FIG. 1, the nozzle structures 20 of the dispensing device 15 may include nozzle structures having any one of various configurations and employing any number of different components, e.g., single and dual capillary electrodes, micro-machined tapered openings, etc. For example, as previously indicated, such nozzle structures may include one or more nozzle structures described in U.S. Pat. No. 6,093,557 or U.S. Patent Application US-2002-0007869-A1. Various types of nozzle structures, and dispensing devices with which they may be used, are shown and described herein. However, nozzle structures described in documents incorporated herein may provide further nozzle structures that may be used according to the present invention and/or may provide additional description regarding the nozzle structures that have also been described generally herein.

Figure 4:
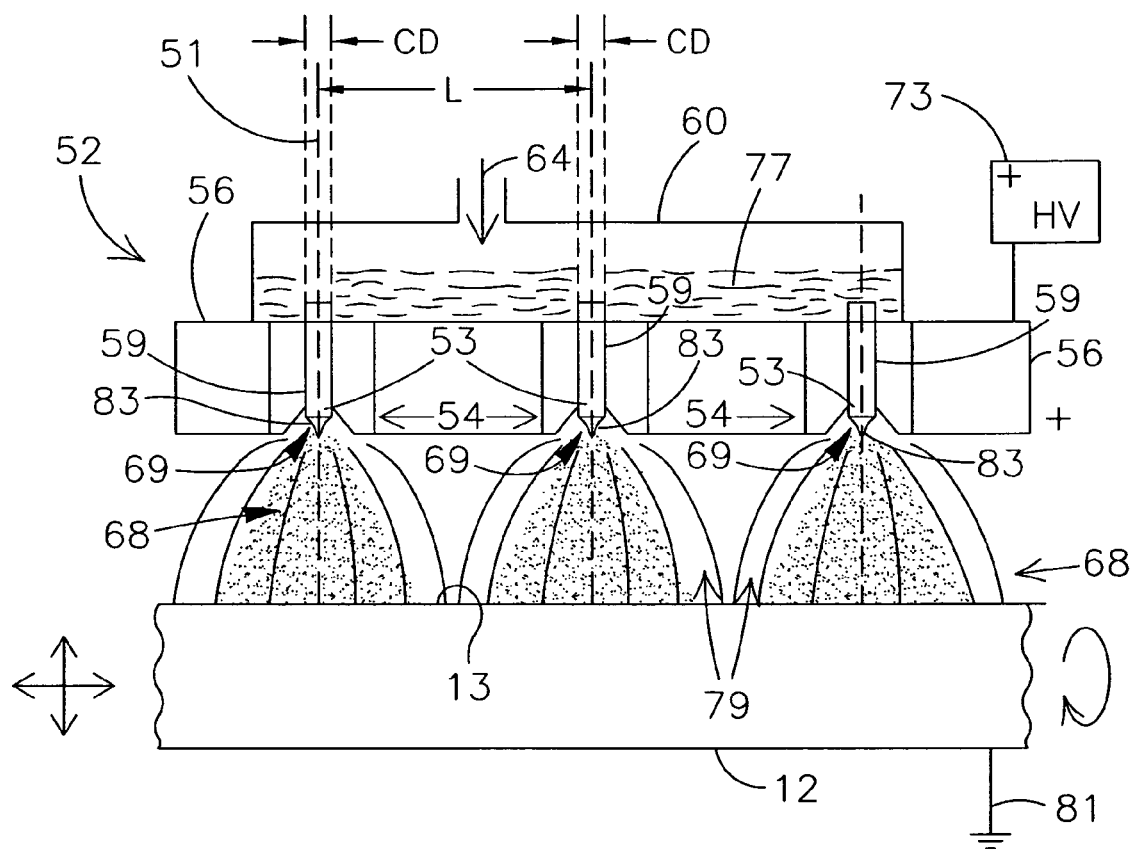
FIG. 4 is a general diagrammatical illustration of one embodiment of an electrospray dispensing device including multiple nozzle structures for use in a coating system shown generally in FIG. 1.

For example, FIG. 4 shows one illustrative embodiment of an electrospray dispensing apparatus 52 that may be employed in the medical device coating system 10 such as shown generally in FIG. 1. The electrospray dispensing apparatus 52 includes one or more nozzle structures 54 for establishing a spray of charged particles 68 from each nozzle structure 54. The electrospray dispensing apparatus 52 includes a source material holding apparatus 60 for providing source material 77 to each of the nozzle structures 54, e.g., simultaneously, for use in establishing the sprays of charged particles 68.

A single electrospray nozzle structure can deliver a controlled feed rate of source material in the establishment of a spray of particle 68 within the envelope of the nozzle structure. This feed rate of source material can be increased by using the multiple nozzle structures 54 bundled together in one or more various configurations. For example, the feed rate may be increased by "n" times with "n" nozzle structures. The present invention, as described further below, enables the employment of as few as one nozzle structure and as many as, for example, 1,000 nozzle structures, e.g., capillary tubes, within a small area, e.g., seven or ten centimeter diameter.

One of various challenges in spraying highly charged nanoparticles from a tightly packed bundle of nozzle structures is to overcome the space charge effect of the nanoparticles from one nozzle structure on other adjacent nozzle structures. With respect to various configurations of multiple nozzle structures, generally, the voltage required to form a cone jet mode for a nozzle structure 54 increases with decreasing internozzle distance. However, it is preferable to operate at a lower voltage because higher voltages may cause arcing between nozzle structures and a second electrode used to form the electric field; such arcing being problematic. Therefore, it may be desirable to have a multiple nozzle structure configuration that can have nozzle structures spaced close together with less internozzle distance, but which does not require a high voltage to establish the cone jet.

As shown in FIG. 4, each nozzle structure 54, e.g., a capillary tube 59, defines an opening 53 extending along an axis 51 and terminating at dispensing end 69. The opening 53 has a cross-section orthogonal to and centered on the axis 51. As used herein, internozzle distance (L) is defined as the distance between the center axis 51 of nozzle structures 54.

The voltage required to obtain a cone jet operation varies based on internozzle distance. Generally, in one embodiment, the voltage required to obtain cone jet operation for a single capillary tube 59 is about 7500 volts. As the internozzle distance (L) decreases, a higher voltage is required to "expel" the highly charged nanoparticles away from the nozzle structure 54 to form the cone jet mode required for spraying nanoparticles. Ultimately, the required voltage reaches the breakdown electric field (approximately 18,000 volts) which defines the closest distance for the internozzle spacing.

The internozzle distance (L) is also affected by the critical dimension (CD) of the opening 53, e.g., the diameter of cross-section of the opening 53 orthogonal to the axis 51 of the nozzle structure 54. For example, as shown in FIG. 4, capillaries 59 are provided along the axis 51 of the nozzle structure 54 with each capillary terminating at a dispensing end 69. The CD for the nozzle structure 54 is the diameter of the opening 53, i.e., the diameter of the cross-section of the opening from which spray is established at the dispensing end 69.

According to the present invention, to avoid the multiple nozzle structures 54 from becoming a single electrode, e.g., arcing from the nozzle structures to the second electrode, a certain internozzle distance (L) must be provided between the nozzle structures 54. Preferably, according to the present invention, the ratio of the internozzle distance (L) to CD, i.e., L/CD, is equal to or greater than 2. In other words, as shown in FIG. 4, preferably, the ratio of the internozzle distance (L) to the diameter of the opening 53 orthogonal to axis 51 is equal to or greater than 2.

Each of the nozzle structures 54 of the electrospray dispensing device 52 provides a charged spray with a high concentration of charged particles. Generally, the concentration of charged particles in the spray is in the range of about $10^5$ particles per cubic centimeter (particles per cc) to about $10^{12}$ particles/cc. Due to the space charge effect, i.e., the effect created by the charge repulsion of charged particles, a spray of substantially dispersed particles having the same polarity charge is provided with the particles distributed substantially uniformly across the spray area, as shown in FIG. 4.

As used herein, the term substantially dispersed particles refers to uniformly and/or nonuniformly sized particles separated by an applied repulsive electrostatic force. Thus, the electrospray process is a consistent and reproducible transfer process. Further, because the charged particles of the spray repel one another, agglomeration of the particles is avoided. This results in a more uniform particle size. "Substantially dispersed" particles is not to be confused with monodisperse particles which involves the general degree of uniformity of the particles sprayed, e.g., the standard deviation of the particles from a nominal size.

Generally, according to the configuration as shown at FIG. 4, the charge is applied by concentration of charge on the spray of particles through evaporation of solution including the material, e.g., active ingredient, in an established electrical field 79. In other words, for example, the source material 77 may be a suspension of active ingredients or a solution including dissolved active ingredients. The suspension or solution is then dispensed from the electrospray dispensing device 52, e.g., active ingredient of microdroplets are dispensed. In other words, the liquid sprayed generally evaporates to concentrate a charge of a liquid portion thereof on the particles, e.g., active ingredient particles, in the fluid composition or suspension being sprayed. This results in the spray of charged particles 68 as described further below.

FIG. 4 generally shows a diagrammatical illustration of the operation of the electrospray dispensing apparatus 52 for establishing charge sprays 68 from each of the nozzle structures 54. Each of the nozzle structures 54 receives a flow of fluid composition from the material source holding apparatus 60. For example, the material source holding apparatus 60 may include a fluid composition 77 suspending drug active ingredients or having active ingredients dissolved therein.

Generally, a conductive material 56, e.g., a conductive plate, positions each of the nozzle structures 54 in a particular configuration. The conductive material 56 is adapted to be connected to a high voltage source 73. Each of the nozzle structures 54 includes a conductive structure, e.g., a capillary tube 59 as illustratively shown in FIG. 4, defining an orifice, e.g., an opening 53 (e.g., a capillary tube opening or an orifice defined in a flooding type chamber, etc.) for receiving a flow of fluid composition 77 therein.

Although various configurations for the source material holding apparatus 60 may be used according to the present invention, preferably a single holding apparatus is used to feed fluid composition 77 to one or more of the nozzle structures 54. One will recognize that any number of different and separate holding apparatus may be used or hold various different fluid compositions and provide different compositions to different nozzle structures 54.

Preferably, the fluid composition 77 may be pushed or pulled through the opening 53 and provided at dispensing end 69 of the nozzle structure 54, e.g., pushed by a pump. Preferably, a compressed gas source represented generally by arrow 64, e.g., an inert source that is non-reactive with the fluid composition 77, is provided to compress the fluid composition 77 and force fluid to flow through openings 53 of the nozzle structures 54. Although, preferably, a compressed gas source 64 is used to provide such fluid composition flow, other methods of providing such flow may also be used. For example, a plate above the fluid composition 77 having a force, e.g., pneumatic force, applied thereto may be used, or syringe pumps for each nozzle structure may be used.

The nozzle structures 54 positioned by and electrically coupled to the conductive structure 56 function as a first electrode of the electrospray dispensing device 52 with the dispensing ends 69 of each nozzle structure being positioned for dispensing charged microdroplets toward medical device 12, or a surface 13 thereof. In the exemplary embodiment of FIG. 4, to set up the electric field 79, the medical device 12 functions as a second electrode structure, e.g., a grounded medical device 12 as shown by ground 81. An electrical potential difference is applied between the first electrode conductive structure 56 and the second electrode or grounded medical device 12 that is electrically isolated from the first electrode. One skilled in the art will recognize that the electrodes may be formed using one or more conductive elements, and such electrodes may take one of various different configurations.

Generally, in operation, a flow of the fluid composition 77 is provided through the openings 53 of the nozzle structures 54, e.g., pushed and/or pulled through the openings 53. A meniscus is formed at the dispensing end 69 where the opening 53 has a diameter in the preferred range of about 6 microns to about 2 millimeters. A potential difference is applied to establish a nonuniform field 79 between the first electrode conductive structure 56 electrically coupled to the nozzle structures 54 and the second electrode (e.g., the medical device 12) connected to ground 81. For example, a high positive voltage may be applied to the first electrode conductive structure 56 with the second electrode medical device 12 being grounded. Further, for example, a voltage difference that provides an electric field intensity of greater than 4 kV/cm is preferably used.

As used herein, nonuniform electric field refers to an electric field created by an electrical potential difference between two electrodes. The nonuniform electric field includes at least some electric field lines that are more locally concentrated at one electrode relative to the other electrode, e.g., more concentrated at the dispensing end 69 relative to the second electrode or a grounded medical device 12. In other words, for example, at least some of the field lines are off axis relative to the longitudinal axis 51 through the center of the opening 53. Further, for example, the grounded medical device 12 is positioned forward of dispensing end 69 and is of a size and/or includes at least a portion that is located at a position away from the longitudinal axis 51. In various embodiments, the second electrode may be one or more ring electrodes, plate electrodes, grounded medical device surfaces, etc. The medical device 12 may still be coated even if a different electrode structure is used to produce the charged particles.

For example, a ring electrode may be positioned forward of the dispensing end 69 to create the electric field for providing highly charged particles in the defined volume in which the medical device is positioned. With the particles provided in the defined volume, another electrical field may be created to move the highly charged particles toward a grounded medical device. As such, it will be recognized that coating the medical device 12 using the coating system 10 shown generally in FIG. 1 may involve providing particles in a defined volume in which the medical device is provided, and thereafter, moving the particles toward the medical device for forming a coating thereon. In addition, alternatively, the particles may be formed and moved toward the medical device for coating thereon simultaneously with their formation. For example, the medical device may be grounded to set up the uniform field for producing the charged particles in the defined volume in which the medical device is provided with the field also providing for the movement of such charged particles towards the medical device 12 so as to form a coating thereon.

In one exemplary embodiment, where the fluid composition includes an active ingredient, the fluid composition 77 is flowed through the opening 53 of the nozzle structures 54. Generally, the fluid composition 77 provided to the opening 53 has an electrical conductivity. As the fluid composition 77 progresses through the opening or orifice 53, the potential difference between the first and second electrodes which creates the electric field therebetween strips the liquid of one polarity of charge, i.e., the negative charge is stripped when a high positive voltage is applied to the electrode 56, leaving a positively charged microdroplet to be dispensed from the dispensing end 69. For example, the meniscus at the dispensing end 69 may form a cone jet for dispensing a spray of microdroplets including the active ingredients when forces of a nonuniform field balance the surface tension of the meniscus. The spray of microdroplets further become more positive in a nonuniform electric field.

As the microdroplets evaporate, the charge of the microdroplets concentrate on the active ingredients resulting in a spray of charged particles. The amount of charge on the microdroplet, and thus the amount of charge on a particle after evaporation, is based at least upon the conductivity of the fluid composition used to spray the microdroplet, the surface tension of the fluid composition, the dielectric constant of the fluid composition, and the feed flow rate thereof. Preferably, the electric charge concentrated on a particular particle is greater than about 30% of a maximum charge that can be held by the microdroplets, without the microdroplet being shattered or torn apart, i.e., greater than about 30% of the Rayleigh charge limit. Preferably, the charge is greater than 50% of the Rayleigh charge limit. At 100%, the surface tension of the microdroplet is overcome by the electric forces causing droplet disintegration. The nonuniform electric field also provides for containment of particles and/or direction for the particles which would otherwise proceed in random directions due to the space charge effect.

One skilled in the art will recognize that the voltages applied may be reversed. For example, the first electrode may be grounded with a high positive voltage applied to the second electrode. In such a case, the particles would have a negative charge concentrated thereon. Further, any other applied voltage configuration providing a nonuniform electric field to establish the charged spray of particles may be used.

The nonuniform electric field can be provided by various configurations. For example, the second electrode may be any conductive material grounded and positioned to establish the formation of a spray 68 from the dispensing ends 69 of the nozzle structures 54, e.g., the second electrode may be a grounded ring electrode, a grounded elongated element positioned in the interior volume of a stent structure, etc. The second electrode may also be located at various positions, such as just forward of the nozzle structures 54, or located farther away from the nozzle structures 54 and closer to medical device 12.

The strength of the field may be adjusted by adjustment of the distance between the first and second electrodes. Different field strengths may result in relatively different areas D upon which particle spray is provided, at least in part due to the space charge effect of the sprays of particles 68. One skilled in the art will recognize that one or more components of the dispensing apparatus 52 may be moved relative to the others, e.g., the medical device relative to the one or more nozzle structures 54 or vice versa, to facilitate adjustment of field strength.

The fluid composition 77 from the holding apparatus 60 is provided to the nozzle structures 54, when operable, under control of, preferably, compressed gas source 64. As described above, the flow may also be controlled with use of a liquid pump (e.g., a syringe pump, a gravity feed pump, a pressure regulated liquid reservoir, etc.), a mass flow controller, or any other flow control devices suitable for feeding source material, e.g., fluid composition 77, to the one or more nozzle structures 54 as would be known to one skilled in the art.

The flow of fluid composition is atomized into microdroplets by the dispensing device 52. Atomization may be provided by any known technique for producing microdroplets, which microdroplets preferably have a nominal diameter of about 10 nanometers or greater, more preferably about 20 nanometers to about 10 micrometers, and even more preferably about 30 nanometers to about 1 micrometer. Preferably, electrostatic atomization is used. However, other atomization devices (e.g., pressure regulated atomizers, ultrasonic nebulizers, hydraulic nozzles, etc.) may provide adequate atomization. As described previously herein, microdroplets having nominal diameters in the range of about 10 nanometers to about 2 microns can be produced by electrospray. Various factors as described in such references affect the produced droplet size. For example, capillary size, liquid feed rate, the dispensing device, surrounding gas properties, etc. One skilled in the art will recognize that such factors and others may be modified to control and produce microdroplets of various desired sizes.

By applying different electrical potential differences between the multiple nozzle structures 54, e.g., capillary tube electrodes 59, and the second electrode, different operating modes can be established. For example, a high positive voltage 73 applied to the capillary tube electrodes via the conductive structure 56 with the grounding of the second electrode medical device 12 provides sprays 68 with a relatively high positive charge. The second electrode 12 in such a case may be provided to ground 81 or may have a negative voltage connected thereto. For example, the voltage applied is limited by the maximum electric field intensity permitted in the medium in which the field is created. For example, arcing will occur in air at an electrical field intensity greater than about 30 kV/cm. However, the allowed electric field intensity can be increased with use of a sheath gas about the nozzle structures, such as $CO_2$, $SF_6$, etc.

With relatively large potential differences being applied, as described herein and in other documents cited herein, pulsating modes or cone jet modes of operation are achieved. In a cone jet mode of operation, a cone shaped liquid meniscus is formed at the dispensing end 69, whereas in the pulsating mode, the shape of a liquid meniscus alternates between a cone shape and a round shape. On the other hand, with relatively low electrical potential differences applied between the capillary tube electrode 59 and the second electrode 12, dripping from the dispensing tip occurs. According to the present invention, a spray from a cone jet 83 formed at the orifice or opening 53 of the capillary tube 59 is preferred.

Although various configurations, as described further below, for the electrospray dispensing apparatus may be suitable, the dispensing apparatus 52 preferably includes capillary tubes 59 made of a suitable material, such as, for example, platinum, silica, etc., for providing the spray 68 from each of the nozzle structures 54, e.g., the capillary tube 59 thereof. For example, the capillary tube may have an outer diameter in the preferred range of about 6 micrometers to about 2.5 millimeters and an inner diameter in the preferred range of about 6 micrometers to about 2 millimeters.

Further, the dispensing apparatus 52 may include a casing about each capillary tube, e.g., a concentric tube, or about the dispensing apparatus 52, e.g., a housing surrounding the spraying portion of the apparatus 52, which may be used to provide a sheath of gas, e.g., $CO_2$, $SF_6$, etc., around the capillary tubes 59 to increase the electrostatic breakdown voltage for the capillary tubes, e.g., to prevent corona discharge. The use of such a sheath of gas is particularly beneficial when the spray is created using a high surface tension liquid, e.g., deionized water.

As previously mentioned, the nonuniform electric field provides for containment of particles and/or direction for the particles which would otherwise proceed in random directions due to the space charge effect; the space charge effect being necessary to provision of monodisperse and noncongl omerated particles. The space charge effect is generally dependent upon the size of the particles and the charge thereon. With the electric field being utilized to move the particles towards the medical device 12 and preventing them from scattering to other locations, the amount of coating material necessary to coat the medical device is substantially reduced.

For example, such a reduction in the amount of coating material can be clearly understood from a comparison between coating according to the present invention and the dipping of a medical device. In the dipping process, a reservoir having the coating material therein must be provided for allowing the device to be dipped. The quantity of material required for dipping is quite substantial.

Contrary to the dipping process, according to the present invention, for example, the concentration of the particles in the defined volume can be controlled with only adequate coating material being present which is to be deposited on the medical device. As such, the quantity of coating material (e.g., DNA or RNA) required is substantially less than required for dipping. In addition, the electric field directs the particles towards the medical device 12 and prevents the particles from depositing on structures surrounding the medical device, e.g., walls of a chamber in which the medical device is positioned, and other structures that may be used in the coating of the medical device such as apparatus associated with the movement of the medical device 12, e.g., either longitudinally or radially.

Further, as described above, as the microdroplets evaporate, the charge of the microdroplets concentrate on the active ingredients resulting in a spray of charged particles. Preferably, the coating material system 10 is configured such that prior to contact with the at least one surface 13 of the medical device 12, a residual particle volume occupied by the evaporated microdroplet includes less than about 20% of a solvent component of the microdroplet sprayed from the dispensing apparatus. However, preferably, some solvent component forms a part of the residual particle volume as the particle contacts the surface 13 of the medical device 12. With some solvent component being a part of the residual particle volume occupied by the evaporated microdroplet, adhesion of the microdroplet (including the particle) to the surface 13 of the medical device 12 may be enhanced. After the microdroplet which includes less than about 20% of the solvent component of the originally sprayed microdroplet has contacted the surface 13 of the medical device, the remainder portion of the solvent evaporates, leaving the particle coated on the surface 13 of the medical device 12. In other words, prior to contact with the at least one surface 13 of the medical device 12, the residual particle volume occupied by the evaporated microdroplet includes some solvent component but less than about 20% of a solvent component contained in the originally sprayed microdroplet.

The amount of evaporation prior to the microdroplet/particle contacting the surface 13 of the medical device 12 may be controlled in any number of different ways. For example, the evaporation may be controlled by the type of solvent used, the distance between the dispensing apparatus and the medical device, the temperature and pressure of a chamber in which the medical device is provided, the size of the microdroplet, etc. The present invention is not limited to any particular method of controlling such evaporation, and various other methods will be apparent to those skilled in the art.

Various configurations of the one or more nozzle structures 54 may be used. For example, the various configurations may include the use of a single capillary tube, multiple capillary tubes bundled in one or more different configurations such as, for example, a pentagon shape, hexagon shape, or other spatial configurations as described in U.S. Patent Application US-2002-0007869-A1, published on 24 Jan. 2002.

Further, for example, capillary tubes made of a suitable material, such as, for example, platinum, silicon, etc., may be used for providing sprays of particles as described herein. Preferably, such capillary tubes are tapered at the tips thereof so as to concentrate the electric field at the tip of each capillary.

Use of capillary tubes may include the use of a single capillary tube as well as dual concentric capillary tubes, such as described in the above-mentioned U.S. Patent Application, US-2002-0007869-A1. For example, dual streams of liquids may be provided from a concentric dual opening capillary dispensing end for establishing a spray from the dispensing apparatus. A dual capillary configuration may be used to spray coated particles of active ingredients or create particles having more than one ingredient. For example, active ingredients may be provided by a first fluid composition through a first opening and a coating material, e.g., a time release polymer, may be provided by a second fluid composition through a second opening. For example, when sprayed, the coating material may encapsulate the active ingredient, at least in part, and the coated particles are then transported for forming a layer on the medical device 12.

Further, such a dual capillary configuration may be used to control conductivity of the particle being sprayed by changing the electrical conductivity of one or more of the liquids being sprayed (e.g., increasing the conductivity of one of the compositions being sprayed such that a higher charge is concentrated on the particle during evaporation).

In addition to the use of fluids with different conductivity, the fluids may also have a different surface tension. For example, a fluid may be flowed through a center capillary with the other fluid being provided in the space between the center capillary and a concentric capillary as described in U.S. Patent Application, US-2002-0007869-A1. With the use of two different fluids having different conductivity and surface tension, hard to spray fluids through the center capillary can be provided at the dispensing ends of the center and concentric capillary. Such spraying is facilitated by, for example, the additional conductivity of the fluid (e.g., an alcohol) in the space surrounding the center capillary such that additional charge is concentrated on the particles sprayed through the center capillary. The spraying is also assisted by the surface tension differences between the fluids as they meet at the dispensing end of the dual capillary configuration to form the cone jet for spraying the fluid through the center capillary.

The dual capillary configuration may be used with any type of source material. For example, the fluids may be active ingredients, biologically active ingredients, excipients, or any other source materials such as those described herein.

Further, the outer fluid may be in a gas form to assist in forming a cone jet or providing components for use in spraying material from the center capillary. Such a gas may also be provided by the center capillary with a fluid provided in the space between the center and concentric capillaries. In such a manner, particles having voids at the center may be formed. Such a particle defining a void, e.g., a bubble, may be beneficial in, for example, a situation where surface area is desired but the quantity of ingredient forming the larger surface area is to be kept to a minimum.

Clearly the present invention is not limited to the use of capillary-type nozzle structures as various suitable nozzle structures may be employed. For example, various other nozzle structures are described generally herein. Any nozzle structure suitable to provide a spray of particles according to the principles described herein may be used, e.g., slits that may provide various cone jets (e.g., with or without posts as described herein), nozzle structures having portions thereof that are integral with portions of other nozzle structures, nozzle structures that form a part of a chamber wall in which a medical device is positioned, radially or longitudinally configured slots such as described herein with particular reference to coating stent structures as shown in FIGS. 11-13, multiple opening nozzle structures (e.g., micromachined nozzle structures that each have dual openings like that of the dual capillary configuration), etc.

Figure 5A:
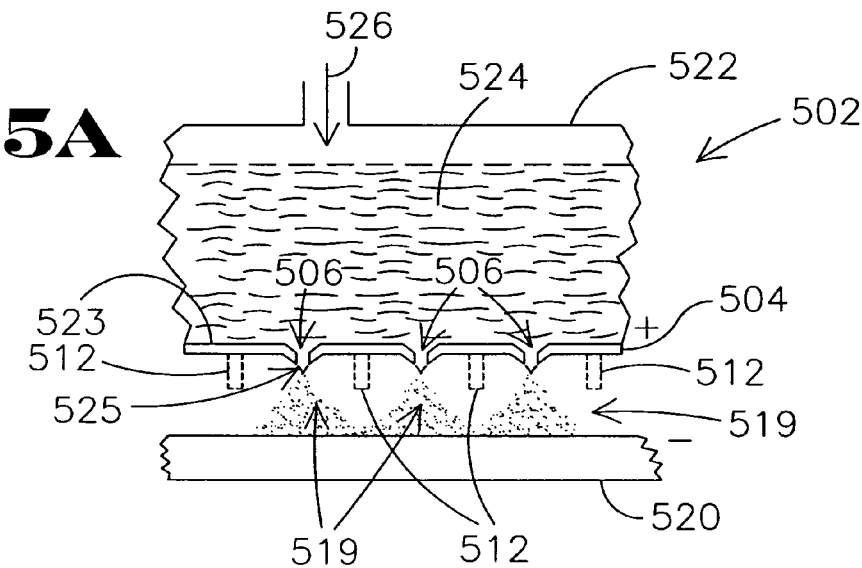
FIGS. 5A and 5B show a general diagrammatical illustration and a more detail view of one portion thereof, respectively, of a configuration of providing multiple electrospray nozzle structures according to the present invention that may be employed in the coating system shown generally in FIG. 1 according to the present invention.
Figure 5B:
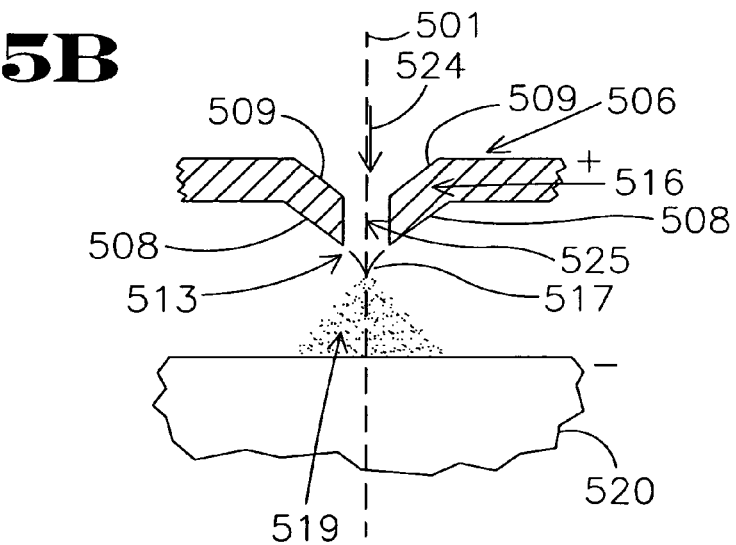

In one of the many different possible nozzle structure implementations, the nozzle structures may be provided using a configuration shown in FIGS. 5A and 5B. An electrospray dispensing apparatus 502 that may be employed in the medical device coating system of FIG. 1 includes one or more nozzle structures 506. The nozzle structures 506 are provided, preferably, by a single integral conductive material 504, e.g., a micro-machined plate. The conductive material or micro-machined plate 504 may form a part, e.g., the bottom surface 523, of fluid composition holding apparatus 522 for containing fluid composition 524 and providing a flow of fluid composition 524 to each of the nozzle structures 506. For example, as described previously herein, a compressed gas source 526 may be used to deliver the fluid composition 524 to each orifice or opening 525 of the nozzle structures 506. With a potential difference provided between the conductive material 504, in which the multiple nozzle structures 506 are formed, and the medical device 520, cone jets 517 (see FIG. 5B) are provided at dispensing ends 513 of the one or more nozzle structures 506 to provide the sprays of particles 519 (e.g., microdroplets that evaporate and concentrate charge on the contained particles used to coat the medical device).

FIG. 5B shows one of the nozzle structures 506 of FIG. 5A in further detail. The nozzle structure 506 includes a tapered portion 516 that defines the orifice or opening 525. The opening 525 of the nozzle structure 506 extends along the axis 501. The tapered portion 516 includes tapered inner surfaces 509, i.e., inner relative to the fluid composition, to receive fluid composition 524 and provide sufficient flow into opening 525. The tapered portion 516 further includes outer tapered surfaces 508. The outer tapered surfaces 508 and inner tapered surfaces 509 are preferably opposing surfaces having a generally parallel configuration. In other words, such tapers are at the same angle relative to the generally plate-like conductive material 504 which lies orthogonal to axis 501. The tapered outer surfaces 508 extend towards the target 520 and terminate at dispensing end 513 at which a cone jet is formed when operating under the applied potential difference.

Figure 6A:
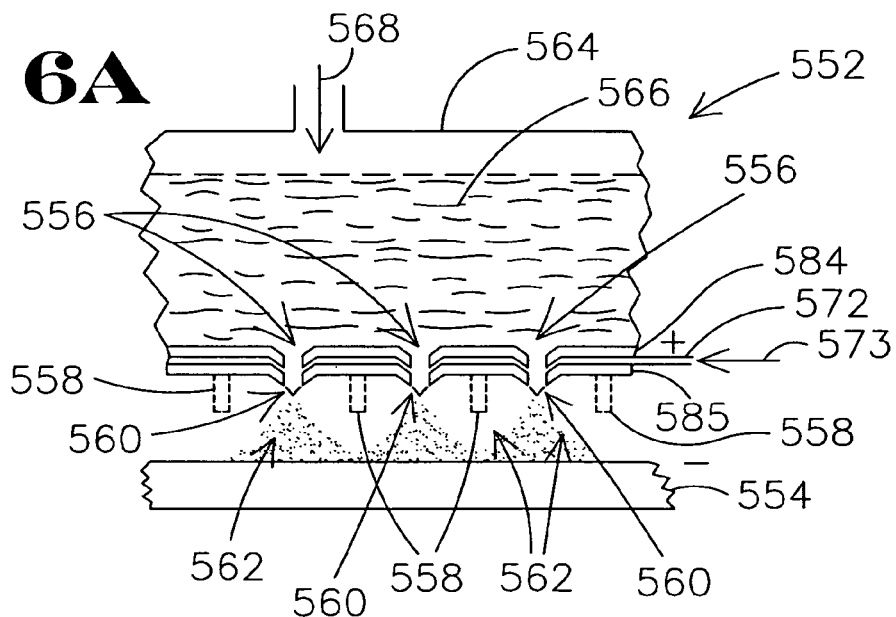
FIGS. 6A and 6B show a general diagrammatical illustration and a more detail view of one portion thereof, respectively, of another alternate embodiment of a configuration for providing multiple electrospray nozzle structures that may be employed in the coating system shown generally in FIG. 1 according to the present invention.
Figure 6B:
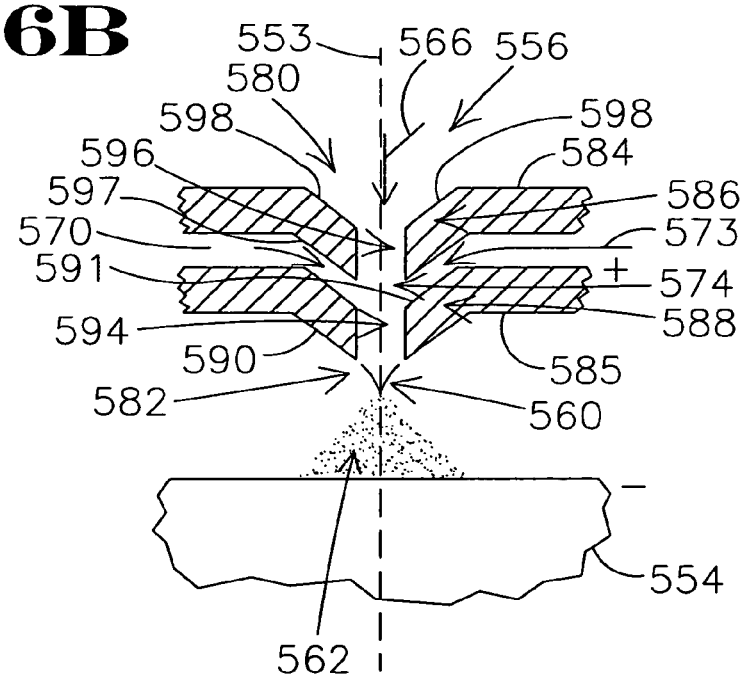

FIGS. 6A and 6B show a diagrammatic illustration of another alternate embodiment of an electrospray dispensing apparatus 552 that includes one or more nozzle structures 556 in a similar manner to that shown in FIGS. 5A and 5B, but having a dual opening configuration. In such a manner, this apparatus may be used in a manner similar to that described herein with respect to concentric capillaries and also as described in U.S. Patent Application, US-2002-0007869-A1.

As shown in FIG. 6A, the dispensing apparatus 552 includes generally two conductive plate-like structures 584 and 585 acting as the first electrode of the device 552. The conductive plate-like structures 584 and 585 are separated to allow for a fluid composition 573 to be provided therebetween from a fluid composition source 572. The plate-like structures 584 and 585 are formed to provide the dual opening nozzle structures 556. Each of the nozzle structures 556 form a cone jet 560 upon application of a suitable potential difference between the first electrode, i.e., the conductive plate structures 584 and/or 585 and the medical device 554. As such, a spray of particles 562 is provided or established at the dispensing ends 582 (see FIG. 6B) of each nozzle structure 556.

Once again under application of compressed gas 568, fluid composition 566 held in holding apparatus 564 is provided for flow through each of the nozzle structures 556. The fluid composition 566 may be the same or different than the fluid composition 573. Preferably, the fluid composition 566 is different than the fluid composition 573. For example, as previously described herein, fluid composition 566 may include an active ingredient for medicinal purposes and the fluid composition 573 may include an excipient or a coating material, such as a time release material, e.g., a polymer. With the use of such fluid compositions, coated particles can be sprayed from each nozzle structure 556 for use in coating the medical device 554.

FIG. 6B shows a more detailed drawing of one nozzle structure 556 employed in the dispensing device 552. As shown in FIG. 6B, first conductive plate structure 584 provides for the definition of an opening 596 through which first fluid composition 566 is provided. The first conductive plate structure 584 and the second plate structure 585 provide for a space or channel 570 therebetween to receive a second fluid composition 573. The second fluid composition 573 meets the first fluid composition 566 at opening 594 defined by the second conductive plate structure 585. Depending on the configuration defining the openings 594, 596 and channel 570, the two fluid compositions may come into contact with each other in either the channel 570 or the opening 594.

The first conductive plate structure 584 includes a tapered portion 586 that defines the opening 596 along axis 553. The tapered portion 586 includes inner tapered surfaces 598, i.e., relative to fluid composition 566, that receive fluid composition 566, and outer surfaces 597 tapered in a manner, preferably like those of inner surfaces 598. The outer surfaces 597 extend towards the medical device 554 and terminate at an outlet 574 into channel 570.

Likewise, conductive plate structure 585 includes tapered portion 588 which defines opening 594 along axis 553. The tapered portion 588 includes inner surfaces 591 that receive the second fluid composition 573 and the first fluid composition 566 provided via outlet 574. The tapered portion 588 further includes outer tapered surfaces 590 that terminate at dispensing end 582 such that when a potential difference is applied between the conductive plate structures 585, 588 and the medical device 554, a cone jet 560 is formed at the dispensing end 582.

It will be recognized that drilling simple holes in conductive plates will not provide for the formation of a cone jet at an orifice thereof. As shown in FIGS. 5 and 6, to form a cone jet at the dispensing ends of the nozzle structures shown therein, each of the nozzle structures must include a protrusion from a plate-like structure. In other words, the tapered portions of the nozzle structure shown in FIGS. 5-6 which provide a protrusion or extension from such plates are required to allow for the formation of a cone jet at the tip of such protruding structures.

As shown in FIGS. 5 and 6, the openings may take the form of a small capillary tube type opening or may take the form of an elongated opening (i.e., a slot). For example, with reference to FIGS. 5A and 5B, the openings 506 and 556 may take the form of elongated openings such as shown in the embodiments for coating a stent structure. For example, one embodiment shown in FIG. 11 uses elongated longitudinal slots that are positioned parallel to an axis along which the stent structure is located. A plurality of the longitudinal slots are located radially about the axis. Radially configured slots are shown in FIG. 12. Such radially configured slots are formed at a distance radially from the axis along which the stent structure is located. A plurality of the radially configured slots (e.g., arcs) are spaced along the axis.

As previously described herein, the particles, e.g., nanoparticles of the sprays established at the dispensing ends of the nozzle structures are generally highly charged which occurs because of an increasingly higher voltage potential applied to the nozzle structure to operate in cone jet mode. Because of the increasingly higher voltage potential, eventually, a corona discharge and voltage breakdown may occur and destroy the cone jet. As shown in FIG. 6A, it is possible to use a separation structure, e.g., structure 558, to isolate each nozzle structure from adjacent nozzle structures to reduce the space charge effect caused by the highly charged nanoparticles. This separation structure technique provides one method of allowing the nozzle structures to be highly packed into a small region.

Various configurations for the separation structure 558 may be used. For example, when capillary tubes are used, separation structures extending from a plate are provided between each of the capillaries and may be used as described in U.S. Patent Application, US-2002-0007869-A1. One skilled in the art will recognize that any form or size of such separation structure may be used as long as suitable isolation of the dispensing ends from each other is provided. Generally, and preferably, the separation structures extend to a point lower than the dispensing end or, in the conjunction with the use of capillaries, the tips thereof. In such a manner, a cone jet is allowed to form at the dispensing end of each nozzle structure.

The separation structure may be made of any insulative material, such as Teflon, plastic, etc. Because the space charge effect is reduced by the separation structure, i.e., the space charge effect between nozzle structures, a more uniform dispersed spray of particles is provided. This is in part due to the lower voltage operation allowed with the use of such separation structure.

It will be recognized by one skilled in the art that the configuration of the separation structure will be, at least in part, dependent upon the structure or configuration of the nozzle structures. In other words, if a rectangular pattern of nozzle structures is utilized, then line type separators may be used. Likewise, if a circular configuration of nozzle structures is used, then such separators may need to be in a type of circular configuration.

Separation structures are shown in FIG. 6A. Such separation extensions 558 are shown as extending from conductive plate structure 585 to separate the nozzle structures 556. Likewise, as shown in FIG. 5A, separation extensions 512 extend from conductive plate structure 504 to separate the nozzle structures 506.

Figure 7B:
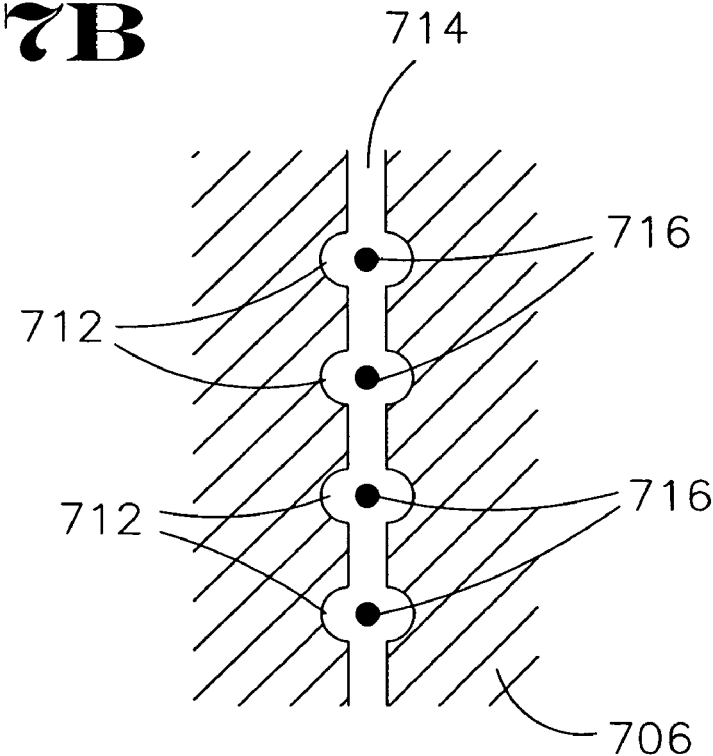
FIGS. 7A and 7B show a general diagrammatical illustration and a more detail view of one portion thereof, respectively, of yet another alternate electrospray multiple nozzle structure that may be employed in the coating system shown generally in FIG. 1 according to the present invention.
Figure 7A:
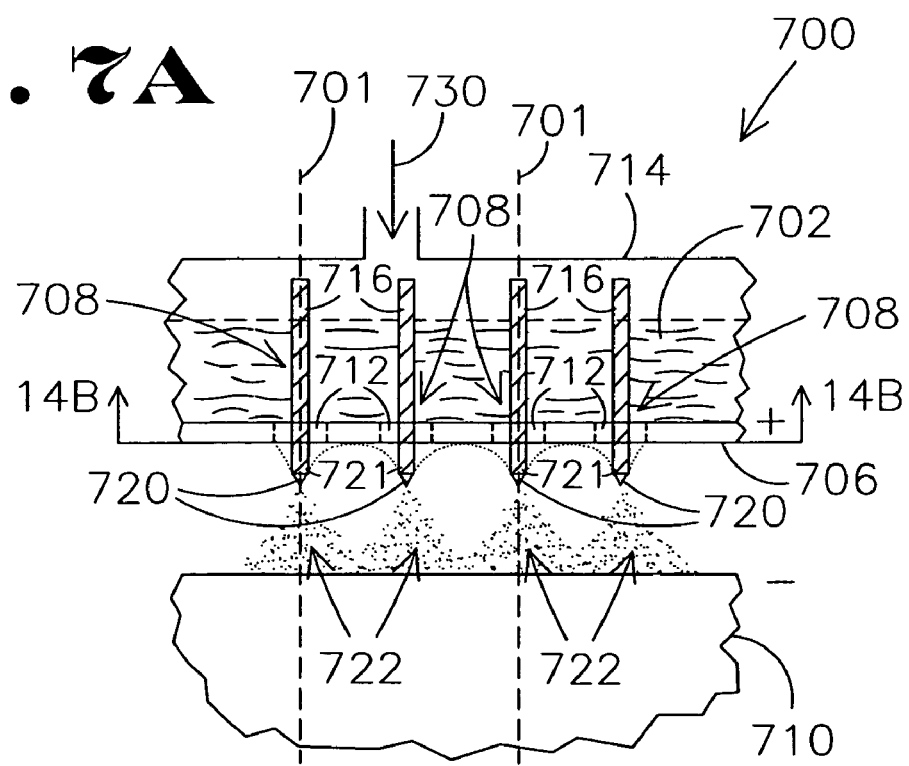

Another alternate dispensing device 700 is shown in FIGS. 7A and 7B. In this alternate configuration, axial posts 716 are used to guide liquid flow. Cone jet formation is facilitated by having the guided post 716 at the center of the cone jet 720. FIG. 7A shows an exemplary side view of the dispensing device 700 and FIG. 7B shows a cross-section of FIG. 7A at line 7B-7B.

As shown in FIGS. 7A and 7B, the dispensing device 700 includes a conductive plate 706 having multiple openings 712, e.g., circular openings, formed therein for use in providing multiple nozzle structures 708. Each opening 712 and the conductive plate 706 generally lie orthogonal to axes 701 of the nozzle structures 708. For machining purposes, such openings may be connected by channel portions 714.

Each of the nozzle structures 708 is formed using one of the openings 712 by providing a post member 716, e.g., a solid post, along the axis 701 through the center of the opening 712. The post member 716 includes a tip 721 that extends a predetermined distance past the conductive plate 706 and through the opening 712 to form the nozzle structure 708.

The plate structure 706 may form a part of fluid composition holding apparatus 704 in which fluid composition 702 is contained. As the fluid composition 702 is pushed through openings 712 forming part of the nozzle structure 708, by or under control of, for example, a compressed gas source 730, the fluid composition 702 follows the post 716. With the appropriate pressure applied by gas source 730 and an electrical potential difference applied between the plate 706 and medical device 710, cone jets 720 are formed at the tips 721 of the post members 716. Sprays of particles 722 are then provided as a result of the cone jets.

The particles in one or more embodiments of the medical device coating system 10 according to the present invention may be provided in one or more different manners according to the present invention. For example, as previously described in many of the embodiments, charged particles are provided by an electrospray apparatus. However, in some embodiments, the particles do not need to be charged particles.

Figure 8A:
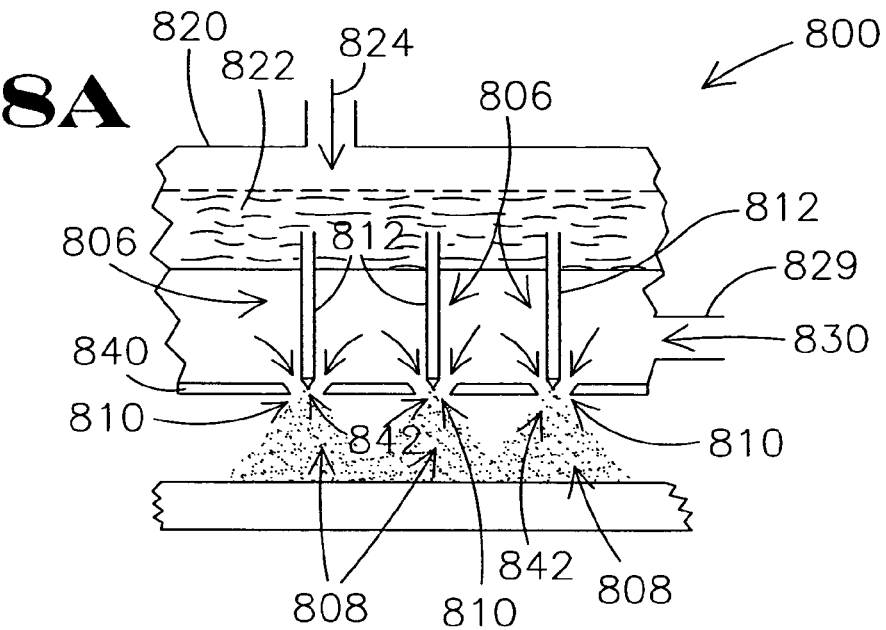
FIGS. 8A and 8B show a general diagrammatical illustration and a more detail view of one portion thereof, respectively, of yet another alternate configuration of a multiple nozzle structure that forms cone jets for spraying particles using air as opposed to electrospray techniques and which may be employed in the medical device coating system of FIG. 1 according to the present invention.
Figure 8B:
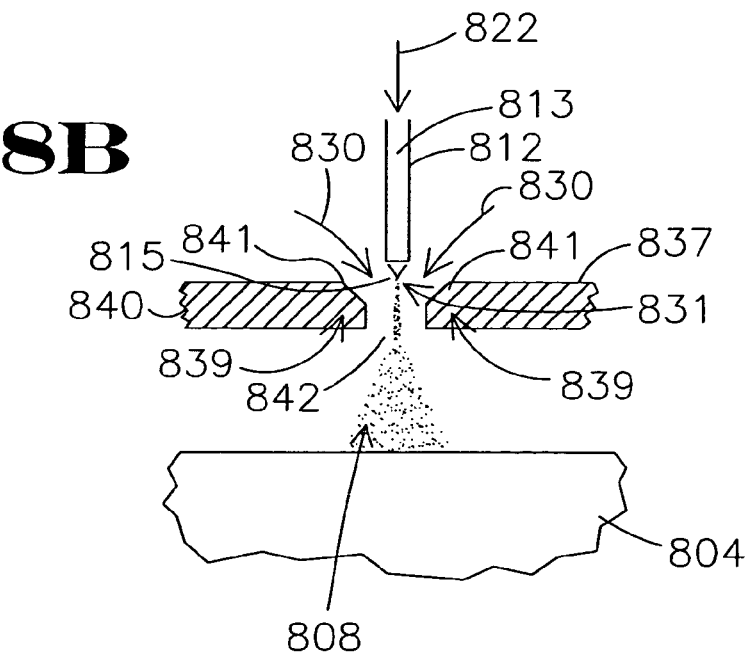

For example, as further described below, use of an thermophoretic effect may be used to move coating particles towards the medical device 12 for coating a surface 13 thereof. In such a case, an alternative to providing a cone jet by electrostatic force is used to form the cone jet. The alternative technique uses an aerodynamic force to provide the cone jet for spraying the particles. FIGS. 8A and 8B show an air dispensing apparatus 800 that employs the use of aerodynamic force in the formation of a cone jet which may be employed in the general embodiment of the medical device coating system shown in FIG. 1.

The air dispensing apparatus 800 includes a plate 840 having openings 842 formed therein for use in providing multiple nozzle structures 806. The multiple nozzle structures 806 of the air dispensing device 800 are provided by positioning a capillary 812 with an end 815 thereof in close proximity to the opening 842 in the plate 840. The capillary 812 generally lies orthogonal to the plate 840. In such a configuration, and as further described below with reference to FIG. 8B, a cone jet 831 can be formed at the dispensing end 810 of the nozzle structure 806 to provide a spray of particles 808 from each nozzle structure 806 that can be moved toward the medical device 804 to form a coating thereon.

To form the cone jet 831, a fluid composition 822 held in holding apparatus 820 is provided into the capillaries 812 under control of, for example, compressed gas source 824. As the fluid composition 822 is pushed through the capillaries 812, a gas source 830, e.g., preferably a compressed gas source, provides compressed gas 830 around the dispensing tip 815 of capillary 812 and through opening 842 of each nozzle structure 806. At least in part, the cone jet mode is provided at the dispensing end 810 of each of the nozzle structures by the compressed gas 830 flowing through opening 842 and around the capillary tube tip 815 as further described below with reference to FIG. 8B.

FIG. 8B shows a more detailed diagram of each nozzle structure 806 of the air dispensing apparatus 800. As shown therein, the capillary tube 812 includes a body portion 813 and the tip 815. Preferably, the tip 815 is slightly tapered. The plate 840, which has the openings 842 defined therein, includes a tapered region 839 defining each opening 842. The tapered region 839 includes inner surfaces 841, i.e., inner relative to the compressed gas 830, provides for receiving the compressed gas 830 and applying aerodynamic force onto the meniscus of fluid composition 822 formed at capillary tube tip 815. The cone jet 831 is formed thereby which provides the spray of particles 808. It would be recognized that the tapered portion 839 may take one of various configurations. For example, such tapered surfaces 841 may include multiple tapers or may be arced, or further, may even include multiple tapered inner and outer surfaces as previously described herein with reference to FIGS. 5-6.

Further, other structures in addition to capillaries may be used to provide the fluid composition in close proximity to the opening for 842. However, preferably, a capillary tube 812 having a tip 815 thereof positioned below the upper surface 837 and in the opening 842 defined in the plate 840 is employed.

Aerodynamic cone jets have been shown to produce particles having a size as small as 70 microns. For example, such cone jets are described in the article entitled "New Microfluidic Technologies to Generate Respirable Aerosols for Medical Application," by Afonso M. Ganan-Calvo, Journal of Aerosol Science, Vol. 30, Suppl. 1, pps. 541-542.

The dual structures, such as those shown in FIG. 6, may be implemented using the aerodynamic structures shown in FIGS. 8A and 8B, as well. For example, multiple openings may be provided for each nozzle structure in a manner similar to that shown in FIGS. 8A and 8B. As such, for example, coated particles may be generated thereby.

As described herein, the present invention is particularly advantageous in coating medical devices such as stent structures (e.g., a stent structure such as that shown generally and diagrammatically in FIG. 2). FIGS. 9A-9E show a holding fixture for use in coating such a stent structure. Further, various embodiments of at least portions of coating systems are described with reference to FIGS. 10-16. Such systems are particularly beneficial in coating stent structures but may also be used in coating other medical devices such as those previously described herein.

FIG. 9A shows a top view of a holding fixture 200 for holding a stent 204 adjacent a dispensing apparatus 202 (e.g., a single or multiple capillary tube electrospray apparatus). As shown in FIG. 9A, the stent 204 is separated from the holding fixture 200 but would be placed on the holding fixture 200 in the region 203 when the coating method is being performed. The holding fixture 200 functions to not only hold the stent structure 204, but also to ground the stent structure 204. FIG. 9B shows a side view of the holding fixture 200 with the stent structure 204 apart from the apparatus 200.

The holding fixture 200 includes an elongated holding structure 206. The holding structure 206 includes a pin holding spindle element 220 as further shown in greater detail in the detailed side view of FIG. 9C. The spindle element 220, e.g., a stainless steel spindle, includes a body member 205 that extends along axis 211 from a threaded first end 223 to a second end 225. The threaded first end 223 of the spindle element 220 is coupled to a corresponding threaded element 210 that is affixed to a platform 201. All the elements of the holding fixture 200 are mounted, either directly or indirectly, to the platform 201.

The spindle element 220 is moveably mounted by moveable holding elements 208 (e.g., bearing structures) to allow for rotation of the spindle holding element 220. Rotation of the spindle element 220 is implemented by a coupling element 216 which couples the spindle element 220 to a motor 212. The motor 212 drives a shaft 217 that is connected via a belt or gear (not shown) to the spindle element 220 at notch 227 (see FIG. 9C). As such, upon rotation of shaft 217, radial motion of spindle element 220 is effected. The spindle element 220 rotates within the holding elements 208. Rotation is permitted by the rotation of threaded first end 223 within the threaded element 210 mounted to the platform 201.

Further, the shaft 217 is moveable in a longitudinal direction along axis 250. Axis 250 lies substantially parallel to axis 211. Such longitudinal motion along axis 250 is translated through the coupling structure 216 to the spindle element 220 effecting motion along axis 211. The spindle element 220 is allowed to move in such a longitudinal manner through openings of holding elements 208.

As such, and as would be recognized by one skilled in the art, the spindle element 220 can be rotated (i.e., radial motion about axis 211) as well as provided with movement along axis 211. The speed of such rotation and longitudinal motion can also be controlled. One skilled in the art will recognize that any type of structure providing such longitudinal and/or radial motion may be used according to the present invention and that the present invention is not limited to this particular structure.

As shown in further detail in FIGS. 9D and 9E, an elongated opening 243 is defined at the second end 225 of the spindle element 220. The opening 243 is sized for receiving a pin holding structure 230. The pin holding structure 230 is shown in further detail in FIG. 9D and generally includes a pin elongated body member 263 that extends from a first end 241 along axis 211 (when mounted) to a second end 257. The pin elongated body member 263 is a conductive elongated body member (e.g., a tungsten pin member). The pin elongated body member 263 may be modified with narrow circumferential rings of conductive or non-conductive material to provide horizontal support for stents of increasing length. Further, the pin elongated body member 263 may also be made non-conductive, so that the stent itself is the only grounded feature in the spray path.

The elongated opening 243 of the spindle element 220 lies along axis 211 and is configured to receive the first end 241 of the pin holding structure 230 and hold the pin holding structure 230 in the elongated opening 243. A slot 245 is provided to accept a clip for holding the pin holding structure 230 within the elongated opening 243 at the second end 225 of the spindle element 220.

Further, the pin holding structure 230 includes a tube element 261 sized to be received over the pin elongated body member 263. The tube element 261 (e.g., a nonconductive tube element) is also sized to allow the stent structure 204 to be positioned thereon. For example, in one embodiment, the tube 261 is inserted over the pin elongated body member 263 of the pin holding structure 230 and thereafter the pin elongated body member 263 and tube element 261 is inserted through the interior volume of the stent structure 204 such that the interior surface of the stent structure 204 is positioned adjacent to the tube element 261.

The pin holding structure 230 further includes a retaining structure 253 at the second end 257 thereof. The retaining structure 253 includes a tapered region 267 (e.g., an electrically conductive portion) for engaging and for use in grounding the stent as further described below. Generally, the retaining structure 253 need only be larger than the stent structure 204 to retain the stent structure on the pin holding structure 230 and include at least a conductive portion which can be used to ground the stent structure 204.

As described above, with the pin elongated boy member 263 and the elongated tube element 261 inserted into the stent structure 204, the interior surface of stent structure 204 is adjacent the nonconductive elongated tube 261. When the pin holding structure 230 is inserted into the elongated opening 243 via end 241, the open end 269 (e.g., a tapered end) of the spindle element 220 contacts the nonconductive tube 261 (e.g., Teflon elongated tube) and forces the tube element 261 to slightly expand such that the stent structure 204 is held stably in position. In other words, the elongated tube element 261 is forced to come in contact with the interior surface of the stent structure 204.

Further, likewise, at least a portion of the stent structure 204 is forced to come in contact with the tapered surfaces 267 of the retaining structure 253. With the stent structure 204 in contact with the conductive material of the retaining structure 253, and the retaining structure 253 in electrical contact with the conductive pin elongated body element 263, the stent structure 204 is easily grounded.

With the stent structure 204 in position, the dispensing apparatus 202 may provide a plurality of particles for coating the stent structure 204. During such coating process, the longitudinal and radial motion of spindle element 220 can be provided for rotating and moving the stent structure 204 radially and longitudinally. In one preferred embodiment, the timing of the rotation of the stent structure 204 about axis 211 and the longitudinal movement of the stent structure 204 along axis 211 can be controlled to coat the stent structure 204 in a single pass. The concentration of coating particles in the region 203 can also be controlled to achieve such single pass coating. Likewise, one or more passes may also be utilized to provide one or more coating layers and/or to provide a laminated type coating on the stent structure 204.

One skilled in the art will recognize that the holding fixture 200 is but one exemplary embodiment of a holding fixture that can be used to locate a stent structure at a particular position during a coating process according to the present invention. Various other holding structures or components thereof are described herein. However, the present invention is not to be taken as being limited to any of the specifically described configurations but only as described in the accompanying claims.

Figure 10A:
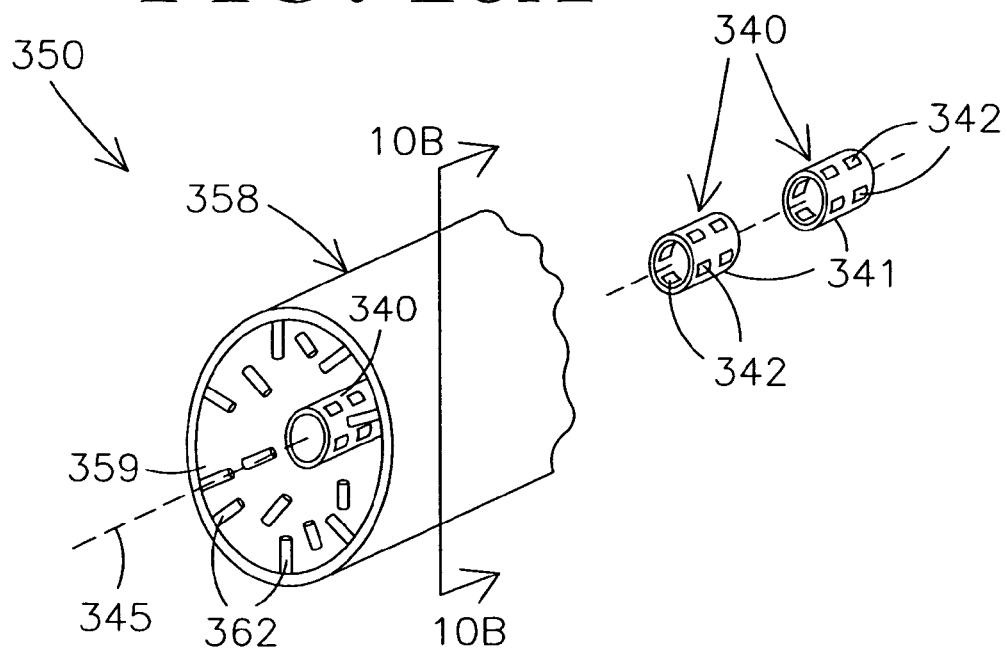
FIGS. 10A and 10B are a perspective view and a cross-section view of a portion thereof, respectively, of one illustrative embodiment of a medical device coating system employing multiple nozzle structures according to the present invention; the system being particularly beneficial in coating stent structures.
Figure 10B:
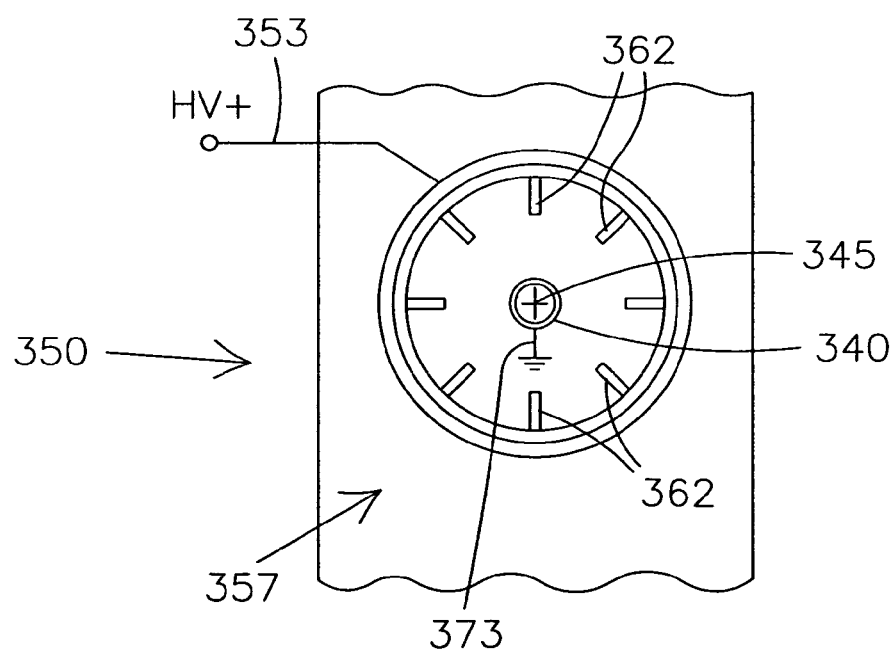

FIG. 10A illustratively shows a perspective view of a stent coating system 350 for coating one or more stent structures 340. FIG. 10B shows a cross-sectional view of a portion of the system 350. Generally, the coating system 350 includes a body member 358, preferably a cylindrical body member that extends along an axis 345 therethrough. Provided at the interior of the cylindrical body member 358 are nozzle structures 362 positioned radially about and also longitudinally along the axis 345. The nozzle structures 362 may be configured as capillary tubes, or may be micro-machined openings such as described herein, or may include any other type of nozzle structures suitable for providing particles according to the present invention. The nozzle structures 362 are preferably configured at the inner surface 359 of the body member 358.

In operation, the stent structures 340 are held within the body member 358 with the axis 345 coinciding with an axis of the stent structures 340. Any one of a number of different types of holding structures or techniques may be used. Various holding structures and techniques are described herein. However, the present invention is not limited to any particular holding structure but is only limited as described in the accompanying claims. Generally, the stent structures 340, as previously described herein, include an open framework of stent material 341. In other words, stent material 341 includes openings 342 between one or more portions thereof.

With the stent structures 340 positioned within the body member 358, the stent structures 340 are grounded as shown by the illustrative grounding symbol 373 in FIG. 10B. With the stent structures 340 grounded and a high voltage 353 applied to the nozzle structures 362, coating material from a coating material source (e.g., a coating material reservoir 357) may be provided such that an electrospray of particles is established within the interior volume of the body member 358. With such particles provided, the electric field between the nozzle structures 362 and the stent structures 340 provide for the movement of the charged particles to form a coating on the stent structures 340.

The spray of charged particles and the movement of such particles towards the stent structure have been described previously herein. As such, further detail about the provision of the charged particles and the movement thereof will not be further described.

One skilled in the art will readily ascertain from the previous description that the nozzle structures 362 and other nozzle structures in the following embodiments may take the form of any one or more of the various different types of nozzle structure configurations described herein. Further, such nozzle structures may be operated in any of the manners as described herein.

The reservoir for holding the coating material in the various embodiments herein may take one of various different types of configurations. For example, the reservoir may be a concentric cylindrical holding chamber for the source material as well as any other different type of configuration with operational elements for providing a feed of the source material to the one or more nozzle structures. For example, pressure may be applied to the source material, various gas streams may be used to assist in providing such source material, etc.

Figure 11A:
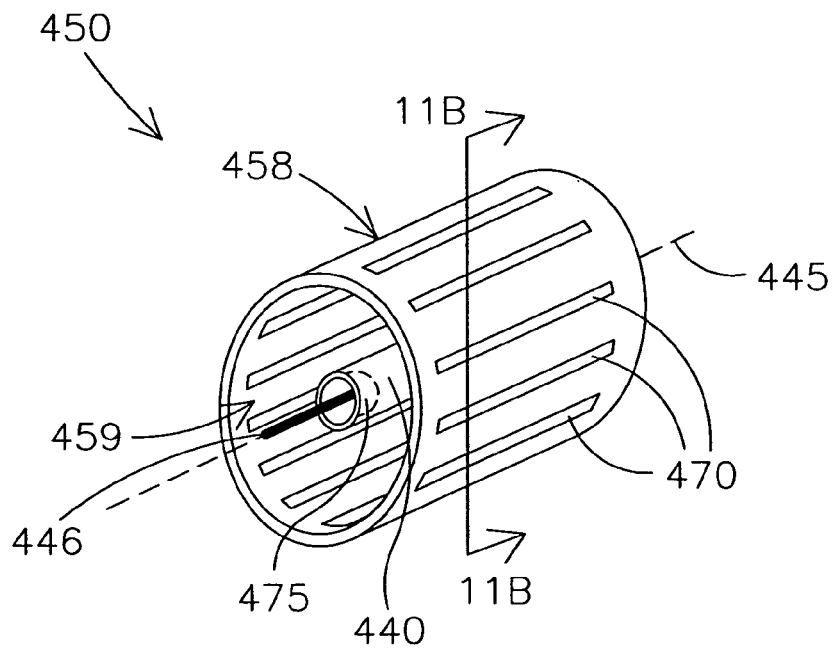
FIGS. 11A and 11B show a perspective view and a cross-section view of a portion thereof, respectively, of another illustrative embodiment of a coating system employing multiple longitudinally configured nozzle structures according to the present invention; the system being particularly advantageous in coating stent structures.
Figure 11B:
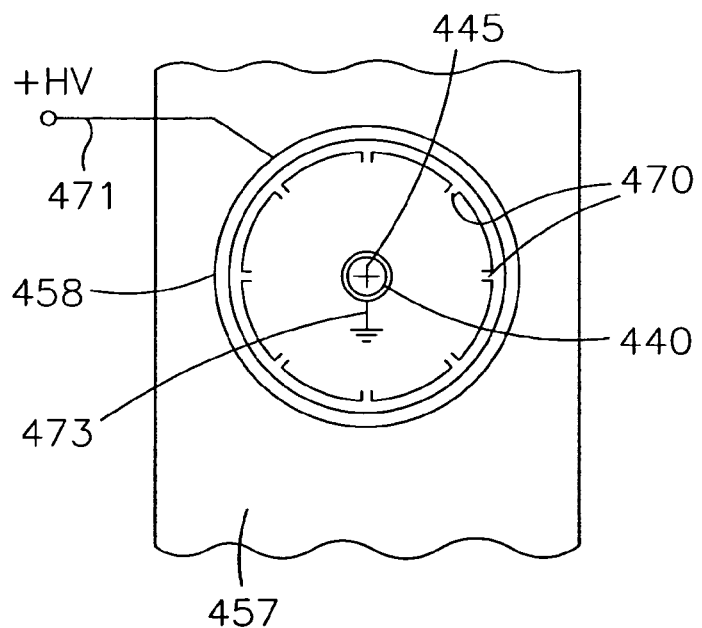
Figure 12:
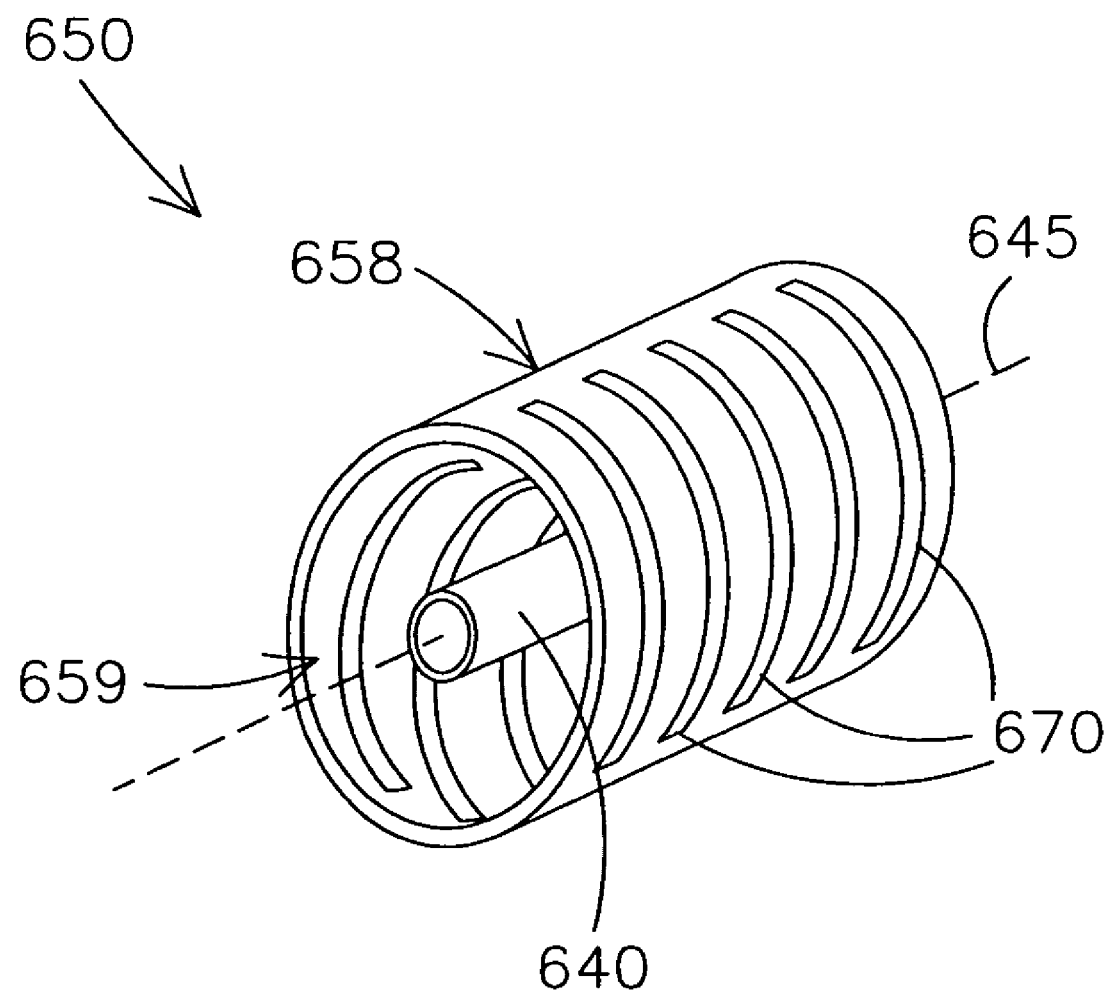
FIG. 12 is a perspective view of yet another alternate illustrative embodiment of a coating system employing multiple radially configured nozzle structures according to the present invention; the system being particularly advantageous in coating stent structures.

FIGS. 11A and 11B show a perspective view and a cross-section view of another stent coating system 450 according to the present invention. The coating system 450 includes a body member 458, preferably a cylindrical body member, extending along axis 445. The cylindrical body member 458 includes longitudinal slots in the body member 458 that extend parallel to axis 445. The longitudinal slots are located in a radial manner about the axis 445 to provide particles within the interior volume 459 of the cylindrical body member 458. A stent structure 440 is positioned within the body member 458 with its axis coincident with axis 445.

The stent structure 440 is held in place by an elongated element 446 (e.g., a wire) with a plug at each end 475 to hold the stent structure 440 in position. The longitudinal slots 470 are preferably equally spaced about the body member 458. As such, each dispensing end of the longitudinal slot 470 is generally of equidistance to the stent structure 440.

FIG. 11B shows an illustrative cross-section view of FIG. 11A taken at line 11B-11B. The cross-section illustration shows a reservoir 457 for holding the coating material that is provided for the spray of particles through the longitudinal slots 470 of the coating system 450. The stent structure 440 is grounded, as shown schematically by ground 473, with the nozzles being held at a high voltage 471 to establish the electric field between the nozzle structures 470 and stent structure 440. One will recognize that there must be some protrusions at the longitudinal slot configuration 470, as previously discussed herein, in order to provide a cone jet suitable for the spray of particles according to the present invention.

FIG. 12 shows yet another alternate portion of a medical device coating system 650 which is substantially similar to that shown in FIGS. 11A and 11B with a cylindrical body member 658 extending along axis 645. However, instead of longitudinal slots being used as part of the nozzle structures as described with reference to FIGS. 11A and 11B, the stent coating system 650 includes radially configured slots 670. The radial slots 670 are configured at a radial distance about axis 645. A plurality of the radial slots 670 are positioned in a direction along the axis 645. With a stent structure 640 positioned such that its axis is coincident with the axis 645, the openings of the nozzle structures formed by the radial slots 670 are equidistant from the stent structure 640.

The radially configured slot configuration may include multiple arc sections of nozzle structures that substantially extend along the entire circumference of the inner surface 659 of the body member 658 or, alternatively, such arc sections may only partially extend along a radial circumference of the inner surface 659. As shown in FIG. 12, two arc sections are configured along the inner circumference on inner surface 659 of the body member 658.

Figure 13A:
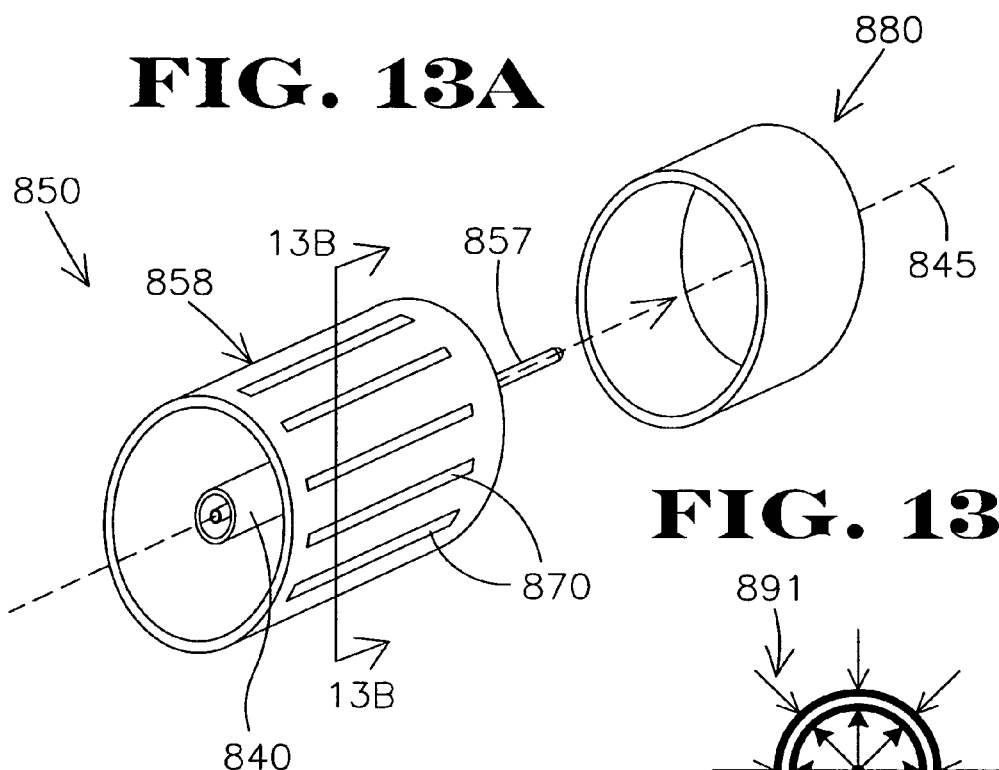
FIGS. 13A-13C show yet another alternate configuration of a medical device coating system according to the present invention.
Figure 13C:
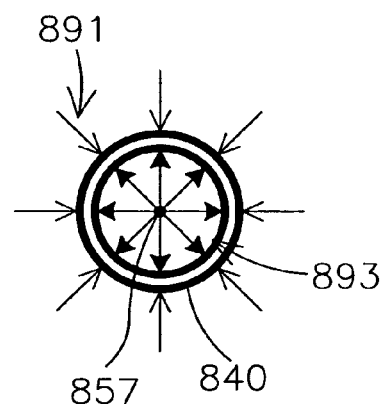
Figure 13B:
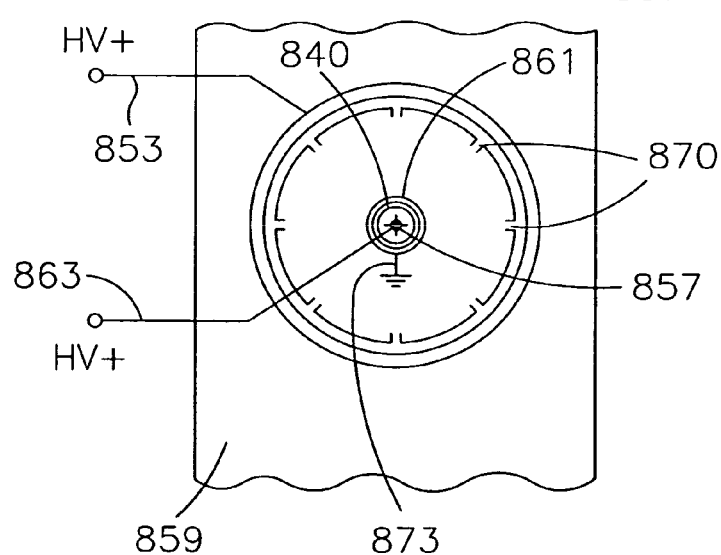

FIGS. 13A-13C illustrate yet another exemplary portion of a stent structure coating system 850 according to the present invention. Essentially, the body member 858 includes longitudinal slots 870 located parallel to axis 845 and spaced radially about the axis 845. This configuration is essentially the same as described with reference to FIGS. 11A and 11B. However, various embodiments of holding a stent structure 840 to be coated located with its axis coincident with axis 845 are shown in FIGS. 13A-13C.

With reference to 13A, one or more additional body members 880 may be positioned along the axis 845 such that the stent structure 840 may be coated with one type of particles in the body member 858 and yet another type of particles in the body member 880. The body member 880 may be configured with nozzle structures (not shown) configured in any manner such as those described herein (e.g., the same or different nozzle structures than used for body member 858).

Further, as shown in FIG. 13A, an elongated support element 857 is used to assist in the coating process and hold the stent structure 840 in position. As shown in FIG. 13B, the stent 840 is positioned with its axis coincident with axis 845 along which the elongated body member 858 extends. Also extending along the axis 845 with its axis coincident with the axis 845 of the stent structure 840 is an elongated support element 857. The elongated support element 857 is positioned in the interior of the stent structure 840.

With the high voltage 853 applied to the nozzle structures 870 and the stent structure grounded (as shown schematically by ground 873), an electric field 891 exists for moving the particles toward the stent structure 840 as shown in FIG. 13C. Further, with an additional high voltage 863 applied to elongated support wire 857 that is conductive, an additional field 893 providing a force opposite to that of electric field 891 is produced. As such, the stent structure 840 is held in a particular position. Further, with proper adjustment of the field strengths, it is possible to control the coating process such that the particles to be coated on the stent structure 840 are substantially maintained on the outer surface of stent structure 840 to form a coating 861 thereon.

As indicated above, this configuration of opposing fields provides not only for the maintenance of the stent structure 840 in a stable position along the elongated support wire 857 but also operates to provide the coating particles about the outer surface of the stent structure 840. As such, the interior surfaces thereof are maintained substantially free of coating material. In certain circumstances, a sheath may even be provided over the stent structure. In other words, not only is the stent structure material of the open framework of material coated with the coating material, but the openings of the open framework material may also having coating material formed thereover to form the sheath. Additional sheath formation will further be described with reference to FIGS. 14A and 14B.

The forces generated by the opposing electric fields may also be provided using other mechanical force techniques. For example, the elongated support element 857 may be a porous capillary that provides an air stream within the body member 858. The air stream provides the force opposing that of the electrical field used to move the particles towards the stent structure 840. Further, the air stream may be used to maintain the stent structure in a stable position.

Each of the above-mentioned techniques may be used to "levitate" the stent structure 840 from the support wire 857 while still maintaining it in a fixed position. Such levitation may provide for a more uniform coating as other holding type fixtures may be eliminated. One skilled in the art will recognize that the air suspension techniques described in U.S. Pat. No. 6,368,658 to Schwartz et al., entitled "Coating Medical Devices Using Air Suspension," issued Apr. 9, 2002, may also be used to hold the stent structure in place for coating according to the present invention.

Figure 14A:
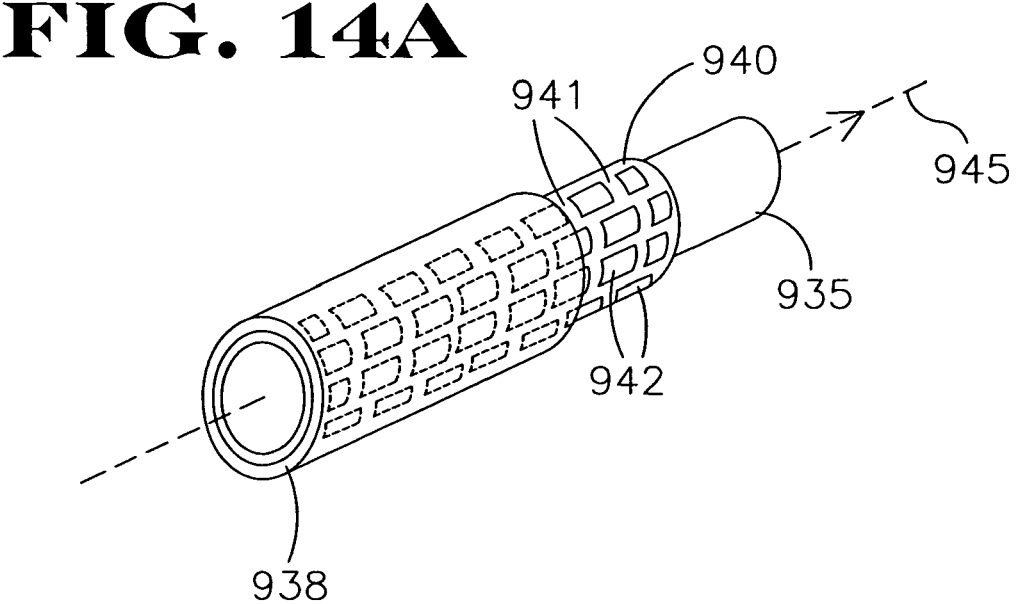
FIGS. 14A and 14B are perspective views used to illustrate a holding structure used during the coating of medical devices, particularly stent structures, according to the present invention.
Figure 14B:
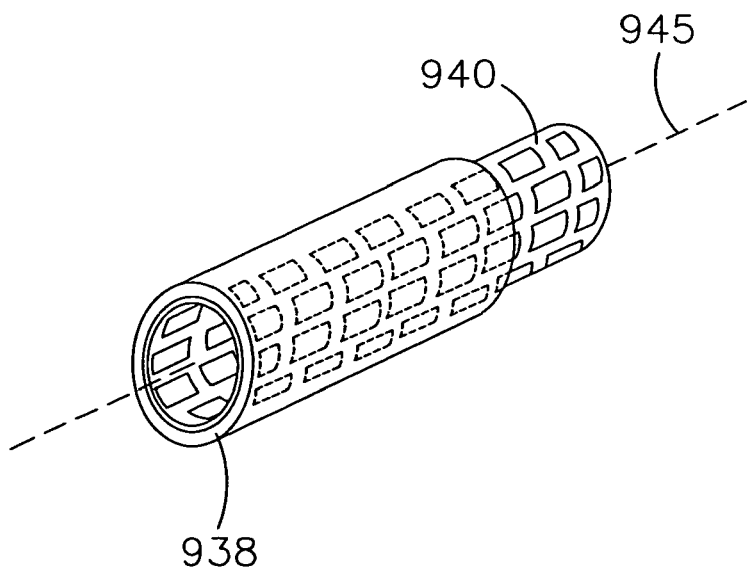

FIGS. 14A and 14B further show a holding structure for holding a stent during a coating process. As shown in FIG. 14A, an elongated element 935 (e.g. a wire or tube) sized for contact with the inner surface of a stent structure 940 is provided. The elongated element 935 preferably is made of a nonconductive material such as Teflon. As such, with the stent structure 940 grounded, coating particles will contact the stent material 941 of the stent structure 940 to form a coating 938 thereover. The coating 938 may be formed not only on the stent material 941 but may also cover openings 942 in the open framework of stent material 941. After the coating 938 has been applied, the element 935 may be removed, leaving the coated stent structure as partially cut-away and shown in FIG. 14B.

In one embodiment of the elongated element 935, the element 935 may be expanded to provide for stretching of the stent material when positioned within the interior volume of the stent structure 940 (e.g., the Teflon tube as shown in the embodiment of FIG. 9). Thereafter, after the coating 938 is applied on the stretched stent structure 948, the force expanding the elongated element 935 may be released and the element 935 removed. The stent structure 940 may then collapse slightly.

Each of the methods of holding the stent structures in position along the axis of the coating system is constructed to prevent the stent structure 940 from sagging. For example, if unsupported, the middle of the stent structure (i.e., the midpoint between a first and second end of the stent structure)

may sag such that all the regions of the stent structure are not equidistant from the axis extending therethrough. With many of the holding configurations described herein, such sagging is eliminated, or at least substantially reduced. Further, in one or more various embodiments of the present invention, if the stent structure is coated in a vertical position, gravity may also prevent sagging.

Figure 15:
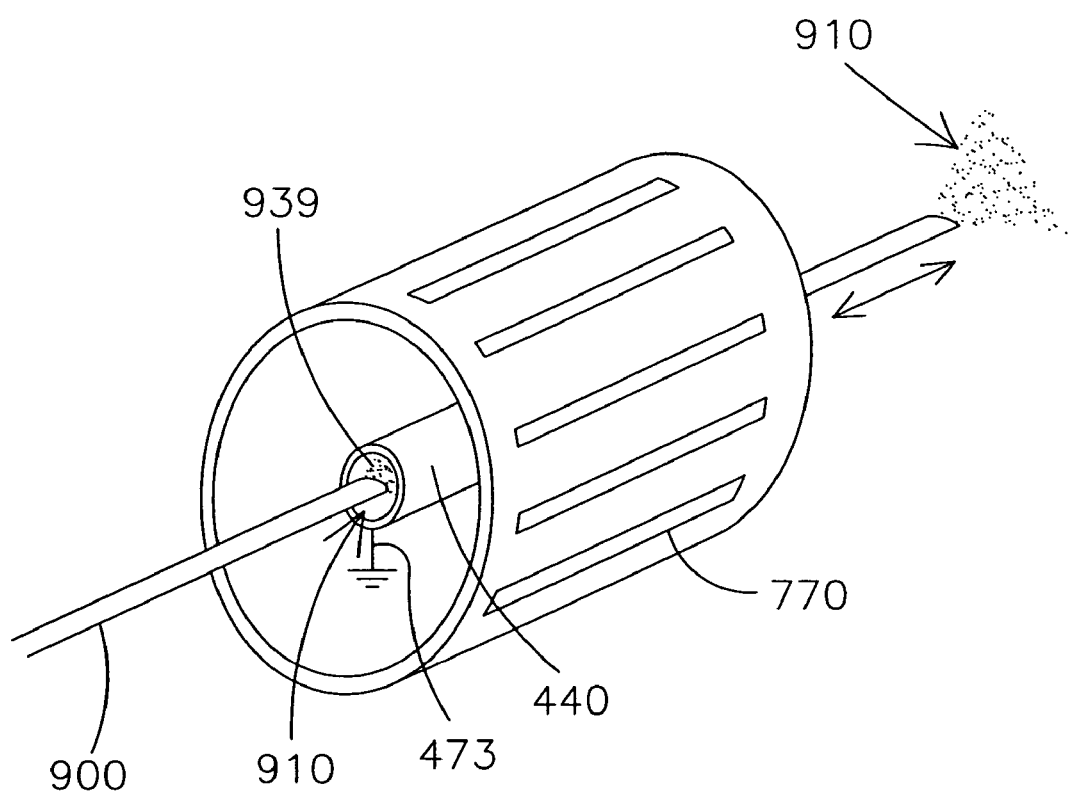
FIG. 15 is a perspective view of yet another alternate configuration of a medical device coating system that may be employed for coating in the interior volume of a medical device (e.g., coating interior surfaces of a stent structure) according to the present invention.

Not only is the present invention advantageous for coating the outer surfaces of stent structures, inner surfaces defining interior volumes of stent structures may also be advantageously coated according to the present invention. As shown in FIG. 15, a coating system for coating an interior surface 939 of a stent structure 940 that defines an interior volume thereof is illustrated.

Generally, the coating system shown in FIG. 15 is essentially the same as that shown in FIGS. 11A and 11B for coating the outer surface of the stent structure 440. However, in addition, an elongated nozzle structure (e.g., a capillary tube 900) may be used to coat an interior surface 939 of the stent structure 440. The stent structure 440 is grounded, as schematically shown by grounding element 473. With the high voltage applied to the capillary tube 900, an electric field is established between the interior surface 939 of stent structure 440 and the capillary tube 900 to form a cone jet and provide a spray of particles 910 into the interior volume of the stent structure 440.

As shown in FIG. 15, the capillary tube 900 is preferably sized to be insertable within the stent structure 440. Further, the capillary tube 900 and/or the stent structure 440 can be moved along the axis 445 to provide a uniform spray on the interior surface 939 thereof. Although FIG. 15 illustrates a single nozzle structure in the form of a capillary 900 providing a spray 910 of particles to coat the interior surface 939, one skilled in the art will recognize that an elongated structure having multiple nozzles yet sized to be received within the stent structure may also be used. Further, any nozzle configuration described herein may also be used to coat the interior surface 939.

Further, an element (e.g., a tube element) may be positioned about the outer surface of the stent structure to hold the stent structure 440 in place during the interior surface coating process shown in FIG. 15. As such, just like the elongated element 935 as described with reference to FIGS. 14A-14B prevents coating on the interior surface, coating may be prevented from deposition on the exterior surface with use of such an element. In such a manner, for example, an interior sheath may be formed on the interior surface.

Figure 16A:
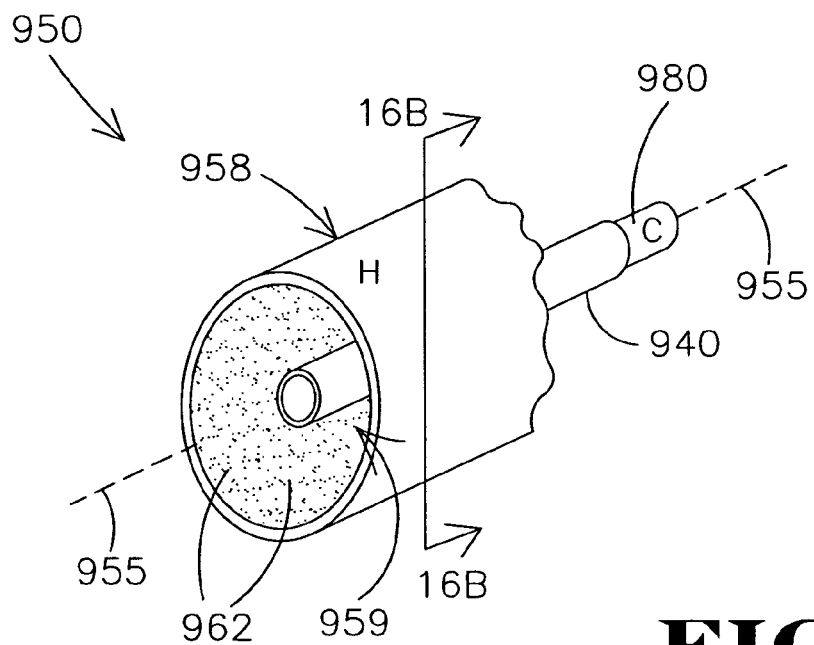
FIGS. 16A and 16B show a perspective view and a cross-section view of a portion thereof, respectively, of another illustrative configuration of a medical device coating system that employs the use of a thermophoretic effect in coating a medical device according to the present invention.
Figure 16B:
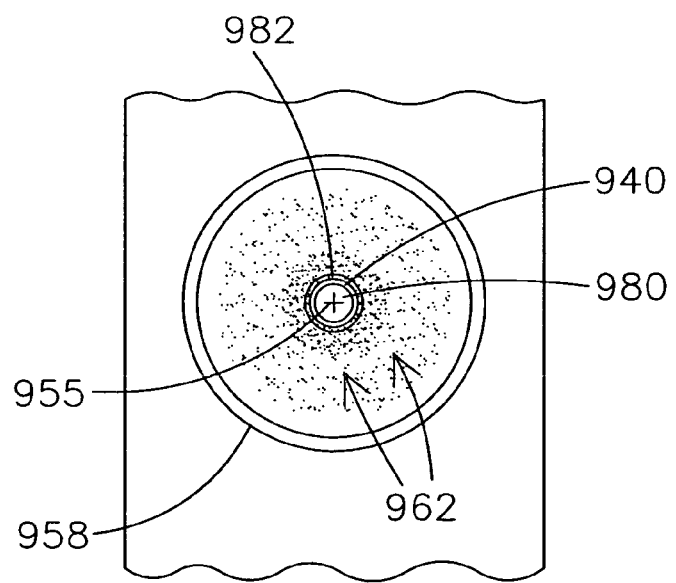

In addition to moving the coating particles towards the stent structure using an electric field, a thermophoretic effect may also be used to move such particles towards a stent structure 940 as shown and illustrated in FIGS. 16A and 16B. As shown therein, thermophoretic forces are used to move particles 962 provided in the interior volume 959 of a body member 958 toward the stent structure 940.

As used herein, the term thermophoretic force denotes the thermal force that is acting on a particle as a result of a temperature gradient associated with the surrounding environment. The effect of this temperature gradient on a given particle may be understood by considering the molecular forces impinging on the particle. Those molecules which strike the particle from a high temperature impart a greater impulse to the particle than those molecules which strike the particle from the low temperature side. In addition, the practitioner skilled in the art will appreciate that concomitant radiation effects may augment these molecular forces. As a result of these and similar effects, the particle feels a net force directing it from the hotter temperature zone to the cooler temperature zone. This is the thermophoretic effect referred to herein.

As shown in FIG. 16A, the coating system 950 includes the body member 958 that extends along axis 955 and is held at a higher temperature than an elongated element 980 that extends through the stent structure 940 (e.g., an element that may be or may not be in contact with the interior surface of the stent structure 940). The stent structure 940 is held such that its axis is coincident with axis 955. As such, a temperature gradient is established and the particles are moved towards the colder elongated element 980 as is shown in the cross-section view of FIG. 16B. With the particles moving towards the colder element 980, a coating 982 is formed on the outer surface of the stent structure 940. The stent structure 940 may be held within the body member 958 using any means previously described herein or any other configuration which preferably holds it at an equidistance from the heated portions of the body member 958. In other words, the temperature gradient is preferably kept equivalent about the stent structure 940 in a radial fashion.

Preferably, as shown in FIGS. 16A and 16B, the elongated element 980 is sized such that it is in contact with the inner surface of a stent structure 940. In such a manner, an effective temperature gradient can be established and particles are prohibited from depositing on the inner surface of the stent structure. In addition, as previously described herein, with an elongated element contacting the inner surface of the stent structure, sagging of the stent structure can be reduced.

All patents, patent documents, and references cited herein are incorporated in their entirety as if each were incorporated separately. This invention has been described with reference to illustrative embodiments and is not meant to be construed in a limiting sense. As described previously, one skilled in the art will recognize that other various illustrative applications may use the techniques as described herein to take advantage of the beneficial characteristics of the particles generated hereby. Various modifications of the illustrative embodiments, as well as additional embodiments to the invention, will be apparent to persons skilled in the art upon reference to this description.

What is claimed is:

1. A system for use in coating at least one surface of a medical device, the system comprising:
   a particle source comprising a first source to provide a first liquid composition and a second source to provide a second liquid composition;
   a holding fixture operable to position a medical device in a defined volume, the defined volume being defined by an enclosure;
   a dispensing device configured to receive source material from the particle source and dispense a plurality of monodisperse coating particles into the defined volume, wherein the dispensing device comprises one or more nozzle structures, wherein each nozzle structure comprises at least a first and second opening terminating at a dispensing end thereof from which a plurality of monodisperse coating particles having an electrical charge applied thereto is dispensed, wherein the first opening is configured to provide a first flow of the first liquid composition at the dispensing end and the second opening is configured to provide a second flow of the second liquid composition at the dispensing end, and further wherein the first opening and second opening are concentric openings; and
   an electrode structure comprising an electrode isolated from the dispensing ends of the one or more nozzle structures, wherein the electrode structure is operable to create a nonuniform electrical field between the dispensing ends of the one or more nozzle structures and the medical device for use in providing the plurality of monodisperse coating particles in the defined volume, wherein the plurality of monodisperse coating particles have a nominal diameter of less than 10 micrometers and a geometrical standard deviation of less than 1.2, and further wherein the nonuniform electric field is operable to assist in moving a plurality of the coating particles towards the at least one surface of the medical device to form a coating thereon.

2. The system of claim 1, wherein the electrode is a grounded medical device.

3. The system of claim 1, wherein the electrode is a ring electrode positioned forward of one or more of the nozzle structures.

4. The system of claim 1, wherein the dispensing device is configured to dispense a spray of microdroplets having an electrical charge associated therewith, wherein each of the microdroplets comprises at least a particle, wherein the electrical charge is concentrated on the particle as the microdroplet evaporates, and further wherein the electrical charge of the microdroplet concentrated on the particle is greater than about 30 percent of the Rayleigh charge limit for the microdroplet.

5. The system of claim 1, wherein the dispensing device is configured to dispense a spray of microdroplets having an electrical charge associated therewith, wherein each of the microdroplets comprises at least a particle, wherein the electrical charge is concentrated on the particle as the microdroplet evaporates, and further wherein the position of the dispensing ends relative to the medical device are such that, prior to contact with the at least one surface of the medical device, a residual particle volume occupied by the evaporated microdroplet comprises less than about 20 percent of a solvent component of the microdroplet.

6. The system of claim 1, wherein the medical device comprises a structure defining an interior volume, wherein the structure comprises at least an interior surface adjacent the interior volume and at least an exterior surface, wherein the holding fixture is operable to position a medical device such that at least one nozzle structure of the dispensing device is operable within the interior volume defined by the structure.

7. The system of claim 6, wherein the electrode structure is operable to create a nonuniform electrical field between the dispensing end of the at least one nozzle structure and the medical device for use in providing the plurality of monodisperse coating particles in the interior volume of the medical device.

8. The system of claim 6, wherein the at least one nozzle structure comprises an elongated element sized to be positioned or moved into the defined interior volume of the medical device.

9. The system of claim 1, wherein the dispensing device comprises a plurality of nozzle structures.

10. The system of claim 1, wherein the holding fixture is configured to hold the medical device in a fixed position within the defined volume.

11. The system of claim 1, wherein the holding fixture is configured for movement of the medical device within the defined volume.

12. The system of claim 1, wherein the holding fixture is configured to receive a stent structure, wherein the stent structure is defined along a stent axis, wherein the stent structure comprises at least an interior surface adjacent a defined interior volume and at least an exterior surface.

13. The system of claim 12, wherein the holding fixture is configured to at least rotate the stent structure about the stent axis.

14. The system of claim 12, wherein the holding fixture is configured to at least move the stent structure linearly along the stent axis.

15. The system of claim 1, wherein the system further comprises a control system operable to control the amount of monodisperse coating particles provided into the defined volume.

16. The system of claim 1, wherein the system further comprises a control system operable to adjust the strength of the nonuniform electrical field.

17. The system of claim 1, wherein the particle source comprises source material for use in providing a plurality of coating particles comprising at least one biologically active ingredient or at least one coated biologically active ingredient.

18. The system of claim 1, wherein the particle source is configured to provide a first flow of a first fluid composition at the first opening and a second flow of a second fluid composition at the second opening.

19. The system of claim 1, wherein the at least one surface of the medical device comprises a conductive surface.

20. The system of claim 1, wherein the at least one surface of the medical device comprises a non-conductive surface.

21. The system of claim 1, wherein the at least one surface of the medical device comprises a polymer.

22. The system of claim 1, wherein the medical device comprises one or more exterior surfaces to be coated that define one or more openings to an interior thereof, and further wherein the medical device comprises one or more interior surfaces to be coated that lie in the interior defined by the one or more exterior surfaces.

23. The system of claim 1, wherein the system further comprises means for charging at least a portion of one or more surfaces of the medical device.

24. The system of claim 1, wherein the system further comprises masking material configured to be positioned proximate the medical device to prevent coating one or more portions thereof.

25. A system for use in coating at least one surface of a stent structure, the system comprising:
a particle source comprising a first source to provide a first liquid composition and a second source to provide a second liquid composition;
a holding fixture operable to position a stent structure defined along a stent axis in a defined volume, the defined volume being defined by an enclosure, wherein the stent structure comprises at least an interior surface adjacent a defined interior volume and at least an exterior surface;
a dispensing device configured to receive source material from the particle source and dispense a plurality of microdroplets having an electrical charge associated therewith from the dispensing ends of the one or more nozzle structures into the defined volume, wherein each of the microdroplets comprises at least a particle, and further wherein the electrical charge is concentrated on the particles as the microdroplets evaporate resulting in a plurality of coating particles, wherein each nozzle structure comprises at least a first and second opening terminating at the dispensing end thereof from which the plurality of microdroplets having an electrical charge applied thereto is dispensed, wherein the first opening is configured to provide a first flow of the first liquid composition at the dispensing end and the second opening is configured to provide a second flow of the second liquid composition at the dispensing end, and further wherein the first opening and second opening are concentric openings; and an electrode structure comprising an electrode isolated from the dispensing ends of the one or more nozzle structures, wherein the electrode structure is operable to create a nonuniform electrical field between the dispensing ends of the one or more nozzle structures and the stent structure for use in providing the plurality of coating particles in the defined volume and moving the plurality of coating particles towards the stent structure to form a coating on the at least one surface thereof.

26. The system of claim 25, wherein the electrode is a grounded stent structure.

27. The system of claim 25, wherein the electrode is a ring electrode positioned forward of one or more of the nozzle structures.

28. The system of claim 25, wherein the plurality of coating particles in the defined volume have a nominal diameter of less than 10 micrometers and a geometrical standard deviation of less than 1.2.

29. The system of claim 25, wherein the plurality of microdroplets comprise a plurality of microdroplets that each have electrical charge associated therewith that is greater than about 30 percent of the Rayleigh charge limit for the microdroplet.

30. The system of claim 25, wherein the position of the dispensing ends relative to the stent structure is such that, prior to contact with the at least one surface of the stent structure, a residual particle volume occupied by the evaporated microdroplet comprises less than about 20 percent of a solvent component of the microdroplet.

31. The system of claim 25, wherein the holding fixture is configured to allow at least one nozzle structure of the dispensing device to be operable within the interior volume defined by the stent structure.

32. The system of claim 31, wherein the electrode structure is operable to create a nonuniform electrical field between the dispensing end of the at least one nozzle structure and the stent structure for use in providing the plurality of coating particles in the interior volume of the stent structure.

33. The system of claim 31, wherein the at least one nozzle structure comprises a capillary tube comprised of a body portion and a tapered capillary tip at the dispensing end of the capillary tube.

34. The system of claim 25, wherein the holding fixture is configured to hold the stent structure in a fixed position within the defined volume.

35. The system of claim 25, wherein the holding fixture is configured for movement of the stent structure within the defined volume.

36. The system of claim 35, wherein the holding fixture is configured to at least rotate the stent structure about the stent axis.

37. The system of claim 35, wherein the holding fixture is configured to at least move the stent structure linearly along the stent axis.

38. The system of claim 25, wherein the dispensing device comprises a plurality of nozzle structures.

39. The system of claim 25, wherein the holding fixture comprises:
an elongated element extending along an axis, the axis of the stent structure coinciding with the axis of the elongated element when received thereon; and
spacing elements operable to maintain a distance between the stent structure and the elongated element.

40. The system of claim 25, wherein the holding fixture comprises an elongated element, wherein the elongated element is sized based on the defined interior volume of the stent structure such that a surface of the elongated element is in direct contact with the interior surface of the stent structure.

41. The system of claim 25, wherein the holding fixture comprises:
a conductive elongated element along the axis of the stent structure, wherein the stent structure and the conductive elongated element are spaced a distance apart; and
a power source configured to create an electric field between the conductive elongated element and the stent structure that is opposite the nonuniform electric field created between the dispensing ends of the nozzle structures and the stent structure.

42. The system of claim 25, wherein the holding fixture comprises an elongated element along the axis of the stent structure, wherein the stent structure and the elongated element are spaced a distance apart, the elongated element configured to provide a gas stream within the defined interior volume of the stent structure.

43. The system of claim 25, wherein the at least one surface of the stent structure comprises a conductive surface.

44. The system of claim 25, wherein the at least one surface of the stent structure comprises a non-conductive surface.

45. The system of claim 25, wherein the at least one surface of the stent structure comprises a polymer.

46. The system of claim 25, wherein the stent structure comprises one or more exterior surfaces to be coated that define one or more openings to an interior thereof, and further wherein the stent structure comprises one or more interior surfaces to be coated that lie in the interior defined by the one or more exterior surfaces.

47. The system of claim 25, wherein the system further comprises means for charging at least a portion of one or more surfaces of the stent structure.

48. The system of claim 25, wherein the system further comprises masking material configured to be positioned proximate the stent structure to prevent coating one or more portions thereof.

49. A system for use in coating at least one surface of a stent structure, the system comprising:
a particle source;
a holding fixture operable to position a stent structure defined along a stent axis in a defined volume, the defined volume being defined by an enclosure, wherein the stent structure comprises at least an interior surface adjacent a defined interior volume and at least an exterior surface;
a dispensing device configured to receive source material from the particle source and dispense a plurality of microdroplets having an electrical charge associated therewith from the dispensing ends of the one or more nozzle structures into the defined volume, wherein each of the microdroplets comprises at least a particle, and further wherein the electrical charge is concentrated on the particles as the microdroplets evaporate resulting in a plurality of coating particles; and
an electrode structure comprising an electrode isolated from the dispensing ends of the one or more nozzle structures, wherein the electrode structure is operable to create a nonuniform electrical field between the dispensing ends of the one or more nozzle structures and the stent structure for use in providing the plurality of coating particles in the defined volume and moving the plurality of coating particles towards the stent structure to form a coating on the at least one surface thereof, wherein the holding fixture comprises:
an elongated substantially non-conductive tube for receiving the stent structure thereon;
an elongated conductive element, wherein at least a portion of the elongated conductive element extends through the elongated substantially non-conductive tube, and further wherein the elongated conductive element comprises a conductive contact section; and
a compression apparatus configured to provide for expansion of the elongated substantially non-conductive tube such that an exterior surface thereof is in contact with at least a portion of the interior surface of the stent structure and such that a portion of the stent structure is in electrical contact with the conductive contact section.

50. The system of claim 49, wherein the holding fixture is configured to at least rotate the stent structure about the stent axis.

51. The system of claim 49, wherein the holding fixture is configured to at least move the stent structure linearly along the stent axis.

52. A system for use in coating at least one surface of a stent structure, the system comprising:
a particle source;
a holding fixture operable to position a stent structure defined along a stent axis in a defined volume, the defined volume being defined by an enclosure, wherein the stent structure comprises at least an interior surface adjacent a defined interior volume and at least an exterior surface;
a dispensing device configured to receive source material from the particle source and dispense a plurality of microdroplets having an electrical charge associated therewith from the dispensing ends of the one or more nozzle structures into the defined volume, wherein each of the microdroplets comprises at least a particle, and further wherein the electrical charge is concentrated on the particles as the microdroplets evaporate resulting in a plurality of coating particles; and
an electrode structure comprising an electrode isolated from the dispensing ends of the one or more nozzle structures, wherein the electrode structure is operable to create a nonuniform electrical field between the dispensing ends of the one or more nozzle structures and the stent structure for use in providing the plurality of coating particles in the defined volume and moving the plurality of coating particles towards the stent structure to form a coating on the at least one surface thereof, wherein the dispensing device comprises a plurality of nozzle structures, wherein the dispensing device comprises an elongated cylindrical body member defining an interior volume thereof along an axis, wherein the holding fixture is operable to position the stent structure along the axis of the elongated cylindrical body member, and further wherein the one or more nozzle structures are positioned radially about the axis of the elongated cylindrical body member and linearly along the elongated cylindrical body member in the direction of the axis thereof.

53. The system of claim 52, wherein each of a plurality of the nozzle structures comprises a capillary tube comprised of a body portion and a tapered capillary tip at the dispensing end of the capillary tube.

54. The system of claim 52, wherein each of a plurality of the nozzle structures comprises a tapered portion used to define an opening, and further wherein at least a part of each of the plurality of the nozzle structures extend from an integral conductive portion associated with the body member.

55. The system of claim 52, wherein each of a plurality of the nozzle structures comprises a solid post along a center axis extending through an opening at the dispensing end.

56. The system of claim 52, wherein each of a plurality of the nozzle structures comprises an elongated radial opening in the body member.

57. The system of claim 52, wherein each of a plurality of the nozzle structures comprises an elongated opening in the body member lying parallel to the axis thereof.

58. A system for use in coating at least one surface of a medical device, the system comprising:
a particle source comprising a first source to provide a first liquid composition and a second source to provide a second liquid composition;
a holding fixture operable to position a medical device in a defined volume, the defined volume being defined by an enclosure;
a dispensing device configured to receive source material from the particle source and dispense a plurality of monodisperse coating particles into the defined volume, wherein the dispensing device comprises one or more nozzle structures, wherein each nozzle structure comprises at least a first and second opening terminating at a dispensing end thereof from which a plurality of monodisperse coating particles having an electrical charge applied thereto is dispensed, wherein the first opening is configured to provide a first flow of the first liquid composition at the dispensing end and the second opening is configured to provide a second flow of the second liquid composition at the dispensing end, and further wherein the first opening and second opening are concentric openings; and
an electrode structure comprising an electrode isolated from the dispensing ends of the one or more nozzle structures, wherein the electrode structure is operable to create a nonuniform electrical field between the dispensing ends of the one or more nozzle structures and the medical device for use in providing the plurality of monodisperse coating particles in the defined volume, wherein the plurality of monodisperse coating particles have a nominal diameter of less than 10 micrometers, and further wherein the nonuniform electric field is operable to assist in moving a plurality of the coating particles towards the at least one surface of the medical device to form a coating thereon.

59. The system of claim 58, wherein the electrode comprises a grounded medical device or a ring electrode positioned forward of one or more of the nozzle structures.

60. The system of claim 58, wherein the dispensing device is configured to dispense a spray of microdroplets having an electrical charge associated therewith, wherein each of the microdroplets comprises at least a particle, wherein the electrical charge is concentrated on the particle as the microdroplet evaporates.

61. The system of claim 58, wherein the medical device comprises a structure defining an interior volume, wherein the structure comprises at least an interior surface adjacent the interior volume and at least an exterior surface, wherein the holding fixture is operable to position a medical device such that at least one nozzle structure of the dispensing device is operable within the interior volume defined by the structure, wherein the electrode structure is operable to create a nonuniform electrical field between the dispensing end of the at least one nozzle structure and the medical device for use in providing the plurality of monodisperse coating particles in the interior volume of the medical device.

62. The system of claim 58, wherein the medical device is a stent structure, and further wherein the holding fixture is configured to rotate the stent structure about the stent axis and/or move the stent structure linearly along the stent axis.

63. The system of claim 58, wherein the medical device is a stent structure, and further wherein the holding fixture is configured to allow at least one nozzle structure of the dispensing device to be operable within the interior volume defined by the stent structure, wherein the electrode structure is operable to create a nonuniform electrical field between the dispensing end of the at least one nozzle structure and the stent structure for use in providing the plurality of coating particles in the interior volume of the stent structure.

64. The system of claim 58, wherein the medical device is a stent structure, and further wherein the holding fixture comprises:
   an elongated element extending along an axis, the axis of the stent structure coinciding with the axis of the elongated element when received thereon; and
   spacing elements operable to maintain a distance between the stent structure and the elongated element.

65. The system of claim 58, wherein the medical device is a stent structure, and further wherein the holding fixture comprises an elongated element, wherein the elongated element is sized based on the defined interior volume of the stent structure such that a surface of the elongated element is in direct contact with the interior surface of the stent structure.

66. The system of claim 58, wherein the medical device is a stent structure, and further wherein the holding fixture comprises an elongated element along the axis of the stent structure, wherein the stent structure and the elongated element are spaced a distance apart, the elongated element configured to provide a gas stream within the defined interior volume of the stent structure.

67. The system of claim 58, wherein the system further comprises a control system operable to adjust the strength of the nonuniform electrical field.

68. The system of claim 58, wherein the particle source comprises source material for use in providing a plurality of coating particles comprising at least one biologically active ingredient or at least one coated biologically active ingredient.

69. The system of claim 58, wherein the plurality of microdroplets comprise a plurality of microdroplets that each have electrical charge associated therewith that is greater than about 30 percent of the Rayleigh charge limit for the microdroplet.

70. The system of claim 58, wherein the dispensing device is configured to dispense a spray of microdroplets having an electrical charge associated therewith, wherein each of the microdroplets comprises at least a particle, wherein the electrical charge is concentrated on the particle as the microdroplet evaporates, and further wherein the position of the dispensing ends relative to the medical device are such that, prior to contact with the at least one surface of the medical device, a residual particle volume occupied by the evaporated microdroplet comprises less than about 20 percent of a solvent component of the microdroplet.

71. The system of claim 58, wherein the at least one surface of the medical device comprises a conductive surface.

72. The system of claim 58, wherein the at least one surface of the medical device comprises a non-conductive surface.

73. The system of claim 58, wherein the at least one surface of the medical device comprises a polymer.

74. The system of claim 58, wherein the medical device comprises one or more exterior surfaces to be coated that define one or more openings to an interior thereof, and further wherein the medical device comprises one or more interior surfaces to be coated that lie in the interior defined by the one or more exterior surfaces.

75. The system of claim 58, wherein the system further comprises means for charging at least a portion of one or more surfaces of the medical device.

76. The system of claim 58, wherein the system further comprises masking material configured to be positioned proximate the medical device to prevent coating one or more portions thereof.

77. A system for use in coating at least one surface of a medical device, the system comprising:
   a particle source;
   a holding fixture operable to position a medical device in a defined volume, the defined volume being defined by an enclosure;
   a dispensing device configured to receive source material from the particle source and dispense a plurality of monodisperse coating particles into the defined volume, wherein the dispensing device comprises one or more nozzle structures, wherein each nozzle structure comprises at least a first and second opening terminating at a dispensing end thereof from which a plurality of monodisperse coating particles having an electrical charge applied thereto is dispensed; and
   an electrode structure comprising an electrode isolated from the dispensing ends of the one or more nozzle structures, wherein the electrode structure is operable to create a nonuniform electrical field between the dispensing ends of the one or more nozzle structures and the medical device for use in providing the plurality of monodisperse coating particles in the defined volume, wherein the plurality of monodisperse coating particles have a nominal diameter of less than 10 micrometers, and further wherein the nonuniform electric field is operable to assist in moving a plurality of the coating particles towards the at least one surface of the medical device to form a coating thereon, wherein the medical device is a stent structure, and further wherein the holding fixture comprises:
   an elongated substantially non-conductive tube for receiving the stent structure thereon;
   an elongated conductive element, wherein at least a portion of the elongated conductive element extends through the elongated substantially non-conductive tube, and further wherein the elongated conductive element comprises a conductive contact section; and
   a compression apparatus configured to provide for expansion of the elongated substantially non-conductive tube such that an exterior surface thereof is in contact with at least a portion of the interior surface of the stent structure and such that a portion of the stent structure is in electrical contact with the conductive contact section.

78. A system for use in coating at least one surface of a medical device, the system comprising:
   a particle source;
   a holding fixture operable to position a medical device in a defined volume, the defined volume being defined by an enclosure;
   a dispensing device configured to receive source material from the particle source and dispense a plurality of monodisperse coating particles into the defined volume, wherein the dispensing device comprises one or more nozzle structures, wherein each nozzle structure comprises at least a first and second opening terminating at a dispensing end thereof from which a plurality of monodisperse coating particles having an electrical charge applied thereto is dispensed; and an electrode structure comprising an electrode isolated from the dispensing ends of the one or more nozzle structures, wherein the electrode structure is operable to create a nonuniform electrical field between the dispensing ends of the one or more nozzle structures and the medical device for use in providing the plurality of monodisperse coating particles in the defined volume, wherein the plurality of monodisperse coating particles have a nominal diameter of less than 10 micrometers, and further wherein the nonuniform electric field is operable to assist in moving a plurality of the coating particles towards the at least one surface of the medical device to form a coating thereon, wherein the medical device is a stent structure, and further wherein the holding fixture comprises:

a conductive elongated element along the axis of the stent structure, wherein the stent structure and the conductive elongated element are spaced a distance apart; and a power source configured to create an electric field between the conductive elongated element and the stent structure that is opposite the nonuniform electric field created between the dispensing ends of the nozzle structures and the stent structure.

* * * * *